(12) United States Patent
Capelli et al.

(10) Patent No.: US 9,968,604 B2
(45) Date of Patent: May 15, 2018

(54) CHROMENE DERIVATIVES AS PHOSHOINOSITIDE 3-KINASES INHIBITORS

(71) Applicant: CHIESI FARMACEUTICI S.p.A., Parma (IT)

(72) Inventors: Anna Maria Capelli, Parma (IT); Matteo Biagetti, Parma (IT); Alessandro Accetta, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days. days.

(21) Appl. No.: 15/079,740

(22) Filed: Mar. 24, 2016

(65) Prior Publication Data
US 2016/0303123 A1  Oct. 20, 2016

(30) Foreign Application Priority Data

Apr. 16, 2015  (EP) .................................... 15163902

(51) Int. Cl.
| | |
|---|---|
| *A61K 31/519* | (2006.01) |
| *A61K 31/52* | (2006.01) |
| *C07D 403/12* | (2006.01) |
| *C07D 405/12* | (2006.01) |
| *C07D 473/34* | (2006.01) |
| *C07D 487/04* | (2006.01) |
| *A61K 31/506* | (2006.01) |

(52) U.S. Cl.
CPC .......... *A61K 31/506* (2013.01); *A61K 31/519* (2013.01); *A61K 31/52* (2013.01); *C07D 403/12* (2013.01); *C07D 405/12* (2013.01); *C07D 473/34* (2013.01); *C07D 487/04* (2013.01)

(58) Field of Classification Search
CPC .... A61K 31/519; A61K 31/52; C07D 403/12; C07D 405/12; C07D 473/34; C07D 487/04
See application file for complete search history.

(56) References Cited

U.S. PATENT DOCUMENTS

| | | |
|---|---|---|
| 6,339,097 B1 | 1/2002 | Festal et al. |
| 2002/0161228 A1 | 10/2002 | Peglion et al. |
| 2005/0020634 A1 | 1/2005 | Terashita et al. |
| 2014/0005247 A1 | 1/2014 | Alarcon Sanchez et al. |

FOREIGN PATENT DOCUMENTS

| | | |
|---|---|---|
| WO | 2008/125694 | 10/2008 |
| WO | 2014/164942 | 10/2014 |

OTHER PUBLICATIONS

Sheridan, R. P., "The Most Common Chemical Replacements in Drug-Like Compounds" J. Chem. Inf. Comput. Sci, 2002, vol. 42, pp. 103-108.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Marwick et al. "Phosphtidylinositol 4-kinase isoforms as targets in respiratory disease" Therapeutic Advances in Respiratory Disease, 2010, vol. 4, issue 1, pp. 19-34. (Year: 2010).*
Extended Search Report in Application No. 15163902.8 dated Jun. 26, 2016.
R. Saiganesh et al., *Tetrahedron Letters,* vol. 30, No. 13, (1989), pp. 1711-1714.
Batchu Chandra Sekhar et al., *Journal of Heterocyclic Chemistry,* vol. 38, No. 2, (2001), pp. 383-386.
Elena Capparelli et al., *Journal of Medicinal Chemistry,* vol. 57, No. 23, (2014), pp. 9983-9994.
Liang Fu et al., *Chem. European Journal,* vol. 21, No. 17 (2015), pp. 6367-6370.
Francesco Leonetti et al., *Journal of Medicinal Chemistry,* vol. 47, No. 27 (2004), pp. 6792-6803.
Jaimala R Ahuja et al., *Synthetic Communications,* vol. 17, No. 16, (1987), pp. 1951-1958.

\* cited by examiner

*Primary Examiner* — Kendra D Carter
(74) *Attorney, Agent, or Firm* — Oblon, McClelland, Maier & Neustadt, L.L.P.

(57) ABSTRACT

Chromene compounds of formula (I), defined herein, inhibit phosphoinositide 3-kinases (PI3K) and are useful for the treatment of disorders associated with a PI3K enzyme mechanism, such as asthma, chronic obstructive pulmonary disease, and idiopathic pulmonary fibrosis.

17 Claims, No Drawings

CHROMENE DERIVATIVES AS PHOSHOINOSITIDE 3-KINASES INHIBITORS

CROSS REFERENCES TO RELATED APPLICATIONS

This application claims priority to European Patent No. 15163902.8, filed on Apr. 16, 2015, which is incorporated herein by reference in its entirety.

BACKGROUND OF THE INVENTION

Field of the Invention

The present invention relates to compounds which inhibit phosphoinositide 3-kinases (hereinafter PI3K). In particular, the present invention relates to compounds that are chromene derivatives, methods of preparing such a compound, pharmaceutical compositions which contain such a compound, and therapeutic uses of such a compound.

Discussion of the Background

In biochemistry, a kinase is a type of enzyme that transfers a phosphate group from a high-energy donor molecule, such as ATP, to a specific substrate, a process referred to as phosphorylation. Specifically, PI3K enzymes are lipid enzyme kinases that can phosphorylate phosphoinositides (PIs) at the 3'-hydroxyl group of the inositol ring (see Panayotou et al., Trends Cell Biol 2:358-60 (1992), which is incorporated herein by reference in its entirety). It is well known that PIs, which are localized in the plasma membranes, can act as second messengers in signaling cascades by docking proteins containing pleckstrin-homology (PH), FYVE, PX and other phospholipid-binding domains (see Vanhaesebroeck B et al., Annu. Rev. Biochem 70, 535-602, 2001; and Katso R et al., Annu. Rev. Cell Dev. Biol. 17, 615-675, 2001, both of which are incorporated herein by reference in their entireties).

Therefore, PIs can act as second messengers in many cellular processes including signal transduction, regulation of membrane trafficking and transport, cytoskeleton organization, cell survival and death, and many other functions.

PIs may be bound to the lipid bilayer of the cell membrane via two fatty acids that are attached to the cytosolic inositol ring via a glycerol phosphate linker. PIs inositol ring can be phosphorylated by PI3K enzymes, leading to the regulation of cellular growth, survival and proliferation. For this reason, PIs phosphorylation by PI3K enzymes is one of the most relevant signal transduction events associated with mammalian cell surface receptor activation (see Cantley L C, Science 296, 1655-7, 2002; and Vanhaesebroeck B et al., Annu. Rev. Biochem 70, 535-602, 2001, both of which are incorporated herein by reference in their entireties).

The PI3K enzymes have been divided into three classes: Class I PI3K, Class II PI3K, and Class III PI3K, on the basis of sequence homology, structure, binding partners, mode of activation, and substrate preference (see Vanhaesebroeck B et al, Exp. Cell Res. 253(1), 239-54, 1999; and Leslie N R et al, Chem. Rev. 101(8), 2365-80, 2001, both of which are incorporated herein by reference in their entireties).

Class I PI3K convert phosphoinositide-(4,5)-diphosphate (PI(4,5)P2) to phosphoinositide-(3,4,5)-triphosphate (PI(3,4,5)P3), which functions as a second messenger. The signaling cascade activated by the increase in intracellular levels of PI(3,4,5)P3 is negatively regulated through the action of 5'-specific and 3'-specific phosphatases (see Vanhaesebroeck B et al., Trends Biochem. Sci. 22(7), 267-72, 1997; Katso R et al., Annu. Rev. Cell Dev. Biol. 17, 615-75, 2001; and Toker A, Cell. Mol. Life Sci. 59(5), 761-79, 2002, all of which are incorporated herein by reference in their entireties).

Class II PI3K enzymes are the most recently identified class of PI3K and their exact function is still unclear.

Class III PI3K enzymes consists of a single family member which is structurally related to Class I PI3K enzymes and appears to be important in endocytosis and vesicular trafficking. However, there is some evidence showing that Class III PI3K may be relevant in immune cell processes, such as phagocytosis and Toll-like receptor (TLR) signalling.

Class I PI3K enzymes can be further divided in class IA and class IB on the basis of their activation mechanisms.

In more detail, Class IA PI3K enzymes comprise three closely related isoforms: PI3Kα, PI3Kβ, and PI3Kδ, while Class IB comprises only the PI3Kγ isoform. These enzymes are heterodimers composed of a catalytic subunit known as p110, with four types: alpha (α), beta (β), delta (δ), and gamma (γ) isoforms, constitutively associated with a regulatory subunit. The first two p110 isoforms (α and β) are ubiquitously expressed and involved in cellular differentiation and proliferation. Consequently, PI3Kα and PI3Kβ enzymes have been extensively studied as targets for the development of new chemotherapeutic agents.

Otherwise, p110δ and p110γ isoforms are mainly expressed in leukocytes and are important in the activation of the immune response, such as leukocytes migration, B and T cells activation and mast cells degranulation. Therefore, PI3Kδ and PI3Kγ isoforms are very relevant in inflammatory respiratory diseases.

Presently, the inhibitors derivatives of PI3K enzymes known in the art could generally inhibit said isoforms (alpha α, beta β, delta δ, and gamma γ isoforms) and they could act on the individual roles played in various diseases by said specific isoforms.

Therefore, specific activity assays of Class IA inhibitors for one specific PI3Kα, PI3Kβ, PI3Kδ, and PI3Kγ isoform over another have been extensively developed in order to discern the suitable profile for the treatment of disorders associated with PI3K enzymes mechanisms. Such disorders could, for example, include respiratory diseases selected from idiopathic chronic cough, cough-variant asthma, cough associated with thoracic tumour or lung cancer, viral or post-viral cough, upper airways cough syndrome (UACS) or post nasal drip cough, or cough associated with gastro-oesophageal reflux disease both acid and non-acid, asthma, chronic bronchitis, chronic obstructive pulmonary disease (COPD), interstitial lung disease, idiopathic pulmonary fibrosis (IPF), congestive heart disease, sarcoidosis, infections (such as whooping cough), viral infections including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia, and central pain.

In view of the number of pathological responses which are mediated by PI3K enzymes, there is a continuing need for inhibitors of PI3K enzymes which can be useful in the treatment of many disorders. Thus, the present invention relates to novel compounds which are inhibitors of PI3Kα, PI3Kβ, PI3Kδ and PI3Kγ isoforms of Class I PI3K enzymes that, for the above reasons, may often have therapeutically desirable characteristics.

Particularly, compounds of the invention may have much more selectivity for the δ isoform or for both the γ and the δ isoforms of PI3K enzyme over other isoforms of the same enzyme.

SUMMARY OF THE INVENTION

Accordingly, it is one object of the present invention to provide novel compounds which inhibit PI3K enzymes.

It is another object of the present invention to provide novel compounds which are inhibitors of PI3Kα, PI3Kβ, PI3Kδ, and PI3Kγ isoforms of Class I PI3K enzymes.

It is another object of the present invention to provide novel methods of preparing such a compound.

It is another object of the present invention to provide novel pharmaceutical compositions which contain such a compound.

It is another object of the present invention to provide novel methods of preventing and/or treating certain diseases and/or conditions by administering such a compound.

These and other objects, which will become apparent during the following detailed description, have been achieved by the inventors' discovery that compounds of formula (I):

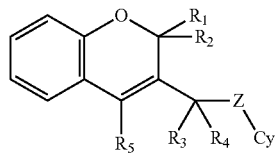

(I)

wherein $R_1$, $R_2$, $R_3$, $R_4$, $R_5$, CY, and Z are as defined below, act as inhibitors of phosphoinositide 3-kinases Thus, the present invention provides the compounds of formula (I).

In another embodiment, the present invention provides processes for the preparation of a compound of formula (I).

In another embodiment, the present invention provides pharmaceutical compositions which comprise a compound of formula (I) either alone or in combination with one or more active ingredient, in admixture with one or more pharmaceutically acceptable carrier.

The present invention further provides a suitable device for the delivery of a pharmaceutical composition which contains a compound of the present invention.

In another aspect, the present invention provides the use of a compound of the present invention for the manufacture of a medicament.

In a further aspect, the present invention provides the use of a compound of the present invention for the preparation of a medicament for the prevention and/or treatment of any disease characterized by phosphoinositide-3-kinase (PI3K) enzyme overactivity and/or wherein an inhibition of PI3K activity is desirable and in particular through the selective inhibition of the delta or of both the delta and the gamma enzyme isoforms over the alfa and beta ones.

Moreover, the present invention provides a method for prevention and/or treatment of any disease wherein a PI3K enzyme inhibition is desirable, said method comprises administering to a patient in need of such treatment a therapeutically effective amount of a compound of the present invention.

In particular the compounds of the present invention alone or combined with other active ingredients may be administered for the prevention and/or treatment of a disease of the respiratory tract characterized by inflammatory airway obstruction such as, for example, cough, asthma, COPD, and IPF.

More particularly, the compounds of the invention are inhibitors of the activity or function of the Class I of PI3K and more specifically, they are inhibitors of the activity or function of PI3Kα, PI3Kβ, PI3Kδ, and/or PI3Kγ isoforms of the Class I PI3K.

Therefore, the compounds of the invention may be useful in the treatment of many disorders associated with PI3K enzymes mechanisms, such as respiratory diseases including asthma, chronic obstructive pulmonary disease (COPD) and cough; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; organ transplantation and in particular in transplant rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain, trigeminal neuralgia, and central pain.

It is understood that the compounds according to the present invention fall in the more general formula:

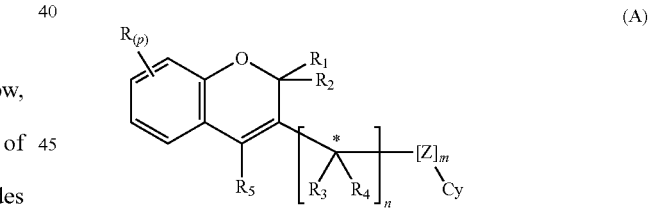

(A)

when m is zero or 1; n is 1; p is zero. Compounds falling in such broader formula are known in the art for example in the International patent Application WO 2014/164942 and in the US patent Application 2014/0005247, both of which are incorporated herein by reference in their entireties.

DETAILED DESCRIPTION OF THE PREFERRED EMBODIMENTS

The present invention is directed to a class of compounds acting as inhibitors of Phosphoinositide 3 Kinases (PI3K). Said class of compounds inhibits the activity or function of the Class I of PI3K and more specifically, they are inhibitors derivatives of the activity or function of PI3Kα, PI3Kβ, PI3Kγ, and/or PI3Kδ isoforms of the Class I PI3K.

The present invention relates to compounds of formula (I):

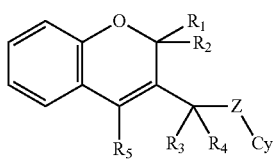

(I)

wherein:

$R_1$ and $R_2$ are both H or are combined to form an oxo group (=O);

$R_3$ and $R_4$, the same or different, in each occurrence are independently selected from the group consisting of H, $(C_1-C_6)$ alkyl, and $(C_1-C_6)$ haloalkyl;

$R_5$ is selected from the group consisting of substituted or unsubstituted aryl and substituted or unsubstituted heteroaryl;

Z is absent or NH; and

Cy is selected from the group consisting of substituted or unsubstituted heteroaryl;

or pharmaceutically acceptable salts thereof.

The term "pharmaceutically acceptable salts," as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium, or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid, and citric acid.

The term "halogen atoms" as used herein includes fluorine, chlorine, bromine, and iodine, preferably chlorine or fluorine.

The term "$(C_1-C_x)$ alkyl" where x is an integer greater than 1, refers to straight-chained or branched-chained alkyl groups wherein the number of constituent carbon atoms is in the range 1 to x. Particularly preferred alkyl groups are methyl, ethyl, n-propyl, isopropyl, and tert-butyl.

The expression "$(C_1-C_x)$ haloalkyl" refers to the above defined "$(C_1-C_x)$alkyl" groups wherein one or more hydrogen atoms are replaced by one or more halogen atoms, which can be the same or different from each other.

Examples of said $(C_1-C_x)$ haloalkyl groups may thus include halogenated, poly-halogenated and fully halogenated alkyl groups, e.g. trifluoromethyl or difluoro methyl groups.

By way of analogy, the terms "$(C_1-C_x)$ hydroxyalkyl" or "$(C_1-C_x)$ aminoalkyl" refer to the above defined "$(C_1-C_x)$ alkyl" groups wherein one or more hydrogen atoms are replaced by one or more hydroxy (—OH) or amino group respectively.

In the present description, unless otherwise provided, the definition of aminoalkyl encompasses alkyl groups substituted by one or more amino groups —$NR_{10}R_{11}$.

With reference to the substituent $R_{10}$ and $R_{11}$ as below defined, it is here further explained that when either $R_{10}$ and $R_{11}$ are taken together with the nitrogen atom they are linked to form a 5 to 6 membered heterocyclic radical, at least one further ring carbon atom in the said heterocyclic radical may be replaced by at least one heteroatom or hetero-group (e.g. N, NH, S, or O) or may bear an -oxo (=O) substituent group. The said heterocyclic radical might be further optionally substituted on the available points in the ring, namely on a carbon atom, or on an heteroatom or hetero-group available for substitution. Thus, examples of said heterocyclic radicals are 1-pyrrolidinyl, 1-piperidinyl, 1-piperazinyl, 4-morpholinyl, piperazin-4yl-2-one, 4-methylpiperazine-1-yl, and 3-(hydroxymethyl)azetidin-1-yl.

The term "$(C_3-C_y)$cycloalkyl", where y is an integer greater than 3, refers to saturated cyclic hydrocarbon groups containing from 3 to y ring carbon atoms. Non limiting examples include cyclopropyl, cyclobutyl, cyclopentyl, cyclohexyl, and cycloheptyl.

The term "aryl($C_1-C_x$)alkyl" refers to an aryl ring linked to a straight-chained or branched alkyl groups wherein the number of constituent carbon atoms is in the range 1 to x, e.g. phenylmethyl (i.e. benzyl), phenylethyl, or phenylpropyl.

The derived expression "$(C_3-C_z)$heterocycloalkyl" refers to saturated or partially unsaturated mono-, bi-, or tri-cyclic $(C_3-C_z)$cycloalkyl groups, wherein z is an integer greater than 3, preferably from 5 to 11 ring atoms in which at least one ring carbon atom is replaced by at least one heteroatom or hetero-group (e.g. N, NH, S, or O). Included in the definition are bridged mono-, bi-, or tri-cyclic ring systems. Non-limiting examples of $(C_3-C_z)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, 1,3-dioxolan-2-yl, 8-azabicyclo[3.2.1]oct-2-en-3-yl radicals and the like. $(C_3-C_z)$heterocycloalkyl groups, as above defined, might be optionally further substituted on the available points in the ring, namely on a carbon atom, or on an heteroatom or hetero-group available for substitution. For example, tetrahydro-pyridinyl groups, when further substituted, might be substituted on the —NH group such as in the following examples: 1-benzyl-1,2,3,6-tetrahydropyridin-4-yl, 1-(cyclopropylmethyl)-1,2,3,6-tetrahydropyridin-4-yl, 1-acetyl-1,2,3,6-tetrahydropyridin-4-yl, and 1-(pyridin-4-yl-methyl)-1,2,3,6-tetrahydropyridin-4-yl;

The term "$(C_2-C_x)$alkenyl" refers to straight or branched, conjugated or non-conjugated, carbon chains with one or more double bonds, in cis or trans configuration, wherein the number atoms is in the range 2 to x.

By way of analogy, the terms "$(C_5-C_y)$ cycloalkenyl", where y is an integer greater than 5, refers to cyclic hydrocarbon groups containing from 5 to y ring carbon atoms and one or two double bonds, wherein the cycloalkenyl might be further optionally substituted by one or more groups, e.g. by amino groups.

The term "$(C_2-C_x)$alkynyl" refers to straight or branched carbon chains with one or more triple bonds wherein the number atoms is in the range 2 to x.

By way of analogy, the term "$(C_2-C_x)$ aminoalkynyl" refer to the above defined "$(C_2-C_x)$ alkynyl" groups wherein one or more hydrogen atoms are replaced by one or more amino group and wherein the amino group might be further optionally substituted by one or more $(C_1-C_6)$ alkyl groups.

The expression "aryl" refers to mono, bi-, or tri-cyclic ring systems which have 6 to 20, preferably from 6 to 15 ring atoms, wherein at least one ring is aromatic.

The expression "heteroaryl" refers to mono-, bi-, or tri-cyclic ring systems with 5 to 20, preferably from 5 to 15 ring atoms, in which at least one ring is aromatic and in which at least one ring atom is a heteroatom or heteroaromatic group (e.g. N, NH, S, or O).

Examples of suitable aryl or heteroaryl monocyclic ring systems include, for instance, phenyl, thienyl (herein also named thiophen-yl or thiophene-yl), pyrrolyl, pyrazolyl, imidazolyl, isoxazolyl, oxazolyl, isothiazolyl, thiazolyl, pyridinyl, pyrimidinyl, pyrazinyl, furanyl radicals, and the like.

Examples of suitable aryl or heteroaryl bicyclic ring systems include naphthalenyl, biphenylenyl, purinyl, pteridinyl, pyrazolopyrimidinyl, benzotriazolyl, quinolinyl, isoquinolinyl, indolyl, isoindolyl, benzothiophenyl, benzodioxinyl, dihydrobenzodioxinyl, indenyl, dihydro-indenyl, dihydrobenzodioxepinyl, benzooxazinyl radicals, and the like.

Examples of suitable aryl or heteroaryl tricyclic ring systems include fluorenyl radicals as well as benzocondensed derivatives of the aforementioned heteroaryl bicyclic ring systems.

The term "$(C_1-C_x)$ alkanoyl", refers to alkylcarbonyl groups (e.g. $(C_1-C_x)$alkyl(CO) where x is an integer greater than 1) wherein the group "alkyl" has the meaning above defined. Non-limiting examples include acetyl, propanoyl, butanoyl.

The expression "arylcarbonyl" refers to aryl-(CO)— groups wherein the group "aryl" has the meaning above defined. Non-limiting example is represented by benzoyl.

The term "aryl $(C_2-C_x)$ alkanoyl" refers to an aryl$(C_2-C_x)$ alkylcarbonyl group where x is an integer greater than 2 wherein aryl and alkyl have the meaning above defined. Non limiting examples are represented by phenylacetyl, phenylpropanoyl, or phenylbutanoyl radicals.

By way of analogy the expressions "aryl$(C_1-C_x)$alkyl", "heteroaryl$(C_1-C_x)$alkyl" and "$(C_3-C_y)$cycloalkyl$(C_1-C_x)$ alkyl" refer to a "$(C_1-C_x)$alkyl" respectively substituted by one or more aryl, heteroaryl or $(C_3-C_y)$cycloalkyl groups, as defined above.

Examples of e.g. aryl$(C_1-C_6)$alkyl include phenylmethyl herein also named benzyl. Examples of e.g. heteroaryl$(C_1-C_6)$alkyl include pyridin-4-ylmethyl. Examples of e.g. $(C_3-C_7)$cycloalkyl$(C_1-C_6)$alkyl include cyclopropylmethyl.

As used herein, the expression "ring system" refers to mono- or bicyclic ring systems which may be saturated, partially unsaturated or unsaturated, such as aryl, $(C_3-C_7)$ cycloalkyl, $(C_3-C_6)$ heterocycloalkyl or heteroaryl.

As used herein an oxo moiety is represented by (O) as an alternative to the other common representation, e.g. (=O). Thus, in terms of general formula, the carbonyl group is herein preferably represented as C(O) as an alternative to the other common representations such as CO, (CO) or C(=O). In general the parenthetical group is a lateral group, not included into the chain, and parentheses are used, when deemed useful, to help distinguish linear chemical formulas. For example, the sulfonyl group —SO₂— might be also represented as —S(O)₂— to distinguish e.g. with respect to the sulfinic group —S(O)O—.

It will be apparent to those skilled in the art that compounds of formula (I) can contain at least one stereogenic center when R₃ and R₄ are different, namely represented in formula (IA) by the carbon atom (*) with an asterisk, and therefore may exist as optical stereoisomers.

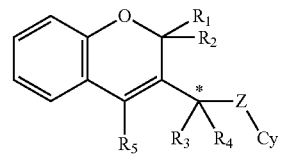

(IA)

Where the compounds according to the present invention have such at least one stereogenic center, they may accordingly exist as enantiomers. Where the compounds according to the present invention possess two or more stereogenic centers, they may additionally exist as diastereoisomers. It is to be understood that all such single enantiomers, diastereoisomers, and mixtures thereof in any proportion are encompassed within the scope of the present invention. The absolute configuration (R) or (S) for carbon (*), when it is a stereogenic center, is assigned on the basis of Cahn-Ingold-Prelog nomenclature rules based on groups' priorities.

Atropisomers are stereoisomers resulting from hindered rotation about single bonds where the steric strain barrier to rotation is high enough to allow for the isolation of the conformers (see Bringmann G et al., Angew. Chemie Int. Ed., 44 (34), 5384-5427, 2005, which is incorporated herein by reference in its entirety).

Oki defined atropisomers as conformers that interconvert with a half-life of more than 1000 seconds at a given temperature (see Oki M, Topics in Stereochemistry 14, 1-82, 1983, which is incorporated herein by reference in its entirety).

Atropisomers differ from other chiral compounds in that in many cases they can be equilibrated thermally, whereas in the other forms of chirality isomerization is usually only possible chemically.

Separation of atropisomers is possible by chiral resolution methods such as selective crystallization. In an atropo-enantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers (substantially free of its corresponding enantiomer) and stereoisomer-enriched atropisomers mixtures are included in the scope of the present invention.

In a preferred embodiment, the present invention is directed to compounds of formula (IA) as above defined wherein R₃ has the same meaning as above except H, R₄ is H and the absolute configuration of the chiral carbon (*) is (R).

In another embodiment, the preferred configuration of the carbon (*) is (S).

In a preferred embodiment, the compounds of formula (I) described in the present invention are present as mixtures of enantiomers and/or diastereoisomers in any proportion.

A first preferred group of compounds is that of formula (I) wherein:

R₁ and R₂ are both H or are combined to form an oxo group (=O);

R₃ is selected from H and $(C_1-C_6)$ alkyl;

R₄ is H;

R₅ is selected from substituted or unsubstituted aryl and substituted or unsubstituted heteroaryl; and Z and Cy are as defined above.

A more preferred group of compounds is that of formula (I) wherein:

$R_1$ and $R_2$ are both H or are combined to form an oxo group (=O);
$R_3$ is selected from H, methyl, ethyl and propyl;
$R_4$ is H;
$R_5$ is selected from phenyl, 2-, 3- or 4-pyridinyl, 5-thiazolyl, 2-, 3-, 4- or 5-thienyl, 1H-pyrazol-4yl, 2-, 4-, 5- or 6-pyrimidinyl, all of which optionally substituted by one or more groups selected from ($C_1$-$C_6$) alkyl, ($C_1$-$C_6$) hydroxyalkyl, substituted or unsubstituted ($C_1$-$C_6$) aminoalkyl; and
Z and Cy are as defined above.

An even more preferred group of compounds is that of formula (I) wherein:

$R_1$ and $R_2$ are both H or combined to form an oxo group (=O);
$R_3$ is selected from H, methyl, ethyl, and propyl;
$R_4$ is H;
$R_5$ is selected from phenyl, 2-, 3-, 4- or 5-thienyl, all of which optionally substituted by one or more groups selected from piperazin-4-ylmethyl, (4-methylpiperazin-1-yl)methyl, piperidin-1-ylmethyl, hydroxymethyl, dimethylaminomethyl, and (3-(hydroxymethyl)azetidin-1-yl)methyl; and
Z, and Cy are as defined above.

A second preferred group of compounds is that of formula (I) wherein:

$R_1$ and $R_2$ are both H or are combined to form an oxo group (=O);
$R_3$ is selected from H, methyl, ethyl and propyl;
$R_4$ is H;
$R_5$ is selected from substituted or unsubstituted aryl, and substituted or unsubstituted heteroaryl;
Z is absent (meaning Z is a bond) or a group NH; and
Cy is an heteroaryl selected from the group of 9H-purin-6-yl, 1H-pyrazolo[3,4-d]pyrimidin-1-yl, 2-, 4-, 5- or 6-pyrimidinyl, which are all optionally substituted by one or more groups selected from halogen, CN, $NR_{10}R_{11}$, optionally substituted aryl and optionally substituted heteroaryl selected from phenyl, 2-, 3-, 4-, 5-, 6-pyridinyl; $R_{10}$, $R_{11}$ the same or different, are at each occurrence independently selected from the group consisting of H, ($C_1$-$C_6$) aminoalkyl, ($C_1$-$C_6$) hydroxyalkyl and ($C_1$-$C_6$) alkyl, or taken together with the nitrogen atom they are linked to, $R_{10}$ and $R_{11}$ may form a 5 to 6 membered heterocyclic radical.

A second more preferred group of compounds is that of formula (I) wherein:

$R_1$ and $R_2$ are both H or combined to form an oxo group (=O);
$R_3$ is selected from H, methyl or ethyl;
$R_4$ is H;
$R_5$ is selected from an aryl which is phenyl, an heteroaryl selected from 2-, 3-, 4- or 5-thienyl, which are all optionally substituted by one or more groups selected from piperazinomethyl (4-methylpiperazin-1-yl)methyl, piperidin-1-ylmethyl, hydroxymethyl, dimethylaminomethyl and (3-(hydroxymethyl)azetidin-1-yl)methyl;
Z is absent or NH; and
Cy is a heteroaryl selected from the group of 9H-purin-6-yl, 1H-pyrazolo[3,4-d]pyrimidin-1-yl, 2-, 4-, 5- or 6-pyrimidinyl; which are all optionally substituted by one or more groups selected from Cl, Br, F, I, CN; $NH_2$, aryl selected from 3-fluoro-5-hydroxyphenyl, 3-chloro-5-hydroxyphenyl and 3-cyano-5-hydroxyphenyl, heteroaryl selected from 6-, 5-, 4-hydroxypyridin-3-yl, (2,2,2-trifluoro-1-(pyridin-3-yl)ethanol)5yl.

A third more preferred group of compounds is that of formula (I) wherein:

$R_1$ and $R_2$ are both H;
$R_3$ is selected from H, methyl or ethyl;
$R_4$ is H;
$R_5$ is selected from substituted or unsubstituted ($C_3$-$C_6$) heterocycloalkyl, substituted or unsubstituted aryl, and substituted or unsubstituted heteroaryl as above defined;
Z is absent; and
Cy is 1H-pyrazolo[3,4-d]pyrimidin-1-yl, optionally and independently substituted by one or more groups selected from halogen, $NR_{10}R_{11}$, ($C_1$-$C_6$) alkyl, substituted or unsubstituted aryl, and substituted or unsubstituted heteroaryl as above defined;
or pharmaceutically acceptable salts or solvates thereof.

Even more preferred group of compounds is that of formula (I) wherein:

$R_1$ and $R_2$ are both H;
$R_3$ is selected from H, methyl or ethyl;
$R_4$ is H;
$R_5$ is selected from the group of phenyl, 2-, 3-, 4- or 5-thienyl, which are all optionally substituted by one or more groups selected from substituted or unsubstituted ($C_1$-$C_6$) aminoalkyl;
Z is absent;
Cy is 1H-pyrazolo[3,4-d]pyrimidin-1-yl, optionally substituted by one or more groups selected independently from halogen, $NR_{10}R_{11}$, phenyl and heteroaryl which is pyridinyl; said phenyl and heteroaryl in their turn further optionally and independently substituted by one or more groups selected from halogen, —OH, —CN; $NR_{10}R_{11}$ ($C_1$-$C_6$)-haloalkyl, ($C_1$-$C_6$) hydroxyalkyl; and
$R_{10}$, $R_{11}$ are as defined above;
or pharmaceutically acceptable salts or solvates thereof.

A fourth preferred group of compounds is that of formula (I) wherein:

$R_1$ and $R_2$ are both H or are combined to form an oxo group (=O);
$R_3$ is selected from H and $C_1$-$C_6$ alkyl;
$R_4$ is H;
$R_5$ is selected from substituted or unsubstituted aryl or substituted or unsubstituted heteroaryl;
Z is absent or NH; and
Cy is substituted or unsubstituted heteroaryl.

A more preferred group of compounds is that of formula (I) wherein:

$R_1$ and $R_2$ are both H or are combined to form an oxo group (=O);
$R_3$ is selected from H and methyl;
$R_4$ is H;
$R_5$ is phenyl or thienyl; said phenyl or thienyl being optionally substituted by a group selected from substituted or unsubstituted ($C_1$-$C_6$) aminoalkyl, or ($C_1$-$C_6$) hydroxyalkyl;
Z is absent or NH; and
Cy is an heteroaryl selected from the group consisting of 9H-purin-6-yl, 1H-pyrazolo[3,4-d]pyrimidin-1-yl and 2-, 4-, 5- or 6-pyrimidinyl, which are all optionally substituted by one, two or three groups selected from CN, $NH_2$, optionally substituted aryl and optionally substituted heteroaryl selected from 3-fluoro-5-hydroxyphenyl 3-chloro-5-hydroxyphenyl, 3-cyano-5-hydroxyphenyl, 3-hydroxy-5-pyridyl and (2,2,2-trifluoro-1-(pyridin-3-yl)ethanol)5yl;

According to specific embodiments, the present invention provides the compounds listed below:

3-((4-amino-3-(3-fluoro-5-hydroxyphenyl)-1H-pyrazolo[3,4-d]pyrimidin-1-yl)methyl)-4-phenyl-2H-chromen-2-one;
3-(1-(4-amino-3-(3-fluoro-5-hydroxyphenyl)-1H-pyrazolo[3,4-d]pyrimidin-1-yl)ethyl)-4-phenyl-2H-chromen-2-one;
3-(4-amino-1-(1-(4-phenyl-2H-chromen-3-yl)ethyl)-1H-pyrazolo[3,4-d]pyrimidin-3-yl)-5-fluorophenol;
5-(4-amino-1-(1-(4-phenyl-2H-chromen-3-yl)ethyl)-1H-pyrazolo[3,4-d]pyrimidin-3-yl)pyridin-3-ol;
3-((9H-purin-6-ylamino)methyl)-4-phenyl-2H-chromen-2-one;
3-(1-(9H-purin-6-ylamino)ethyl)-4-phenyl-2H-chromen-2-one;
N-((4-phenyl-2H-chromen-3-yl)methyl)-9H-purin-6-amine;
4-amino-6-((4-phenyl-2H-chromen-3-yl)methylamino)pyrimidine-5-carbonitrile;
4-amino-6-(1-(4-phenyl-2H-chromen-3-yl)ethylamino)pyrimidine-5-carbonitrile;
1-(5-(4-amino-1-(1-(4-phenyl-2H-chromen-2-yl)ethyl)-1H-pyrazolo[3,4-d]pyrimidin-3-yl)pyridin-3-yl)-2,2,2-trifluoroethan-1-ol;
3-(4-amino-1-(1-(4-phenyl-2H-chromen-2-yl)ethyl)-1H-pyrazolo[3,4-d]pyrimidin-3-yl)-5-hydroxybenzonitrile;
3-(4-amino-1-(1-(4-phenyl-2H-chromen-2-yl)ethyl)-1H-pyrazolo[3,4-d]pyrimidin-3-yl)-5-chlorophenol;
3-(4-amino-1-(1-(4-(5-((4-methylpiperazin-1-yl)methyl)thiophen-2-yl)-2H-chromen-3-yl)ethyl)-1H-pyrazolo[3,4-d]pyrimidin-3-yl)-5-fluorophenol;
3-(4-amino-1-(1-(4-(5-((dimethylamino)methyl)thiophen-2-yl)-2H-chromen-3-yl)ethyl)-1H-pyrazolo[3,4-d]pyrimidin-3-yl)-5-fluorophenol;
3-(4-amino-1-(1-(4-(5-(hydroxymethyl)thiophen-2-yl)-2H-chromen-3-yl)ethyl)-1H-pyrazolo[3,4-d]pyrimidin-3-yl)-5-fluorophenol;
5-(4-amino-1-(1-(4-(5-((dimethylamino)methyl)thiophen-2-yl)-2H-chromen-3-yl)ethyl)-1H-pyrazolo[3,4-d]pyrimidin-3-yl)pyridin-3-ol,
and pharmaceutical acceptable salts thereof.

The compounds of formula (I) including all the compounds here above listed can be generally prepared according to the procedure outlined in the schemes shown below using generally known methods.

In one embodiment of the present invention, according to Scheme 1, compound (Va), wherein $R_1=R_2=R_3=R_4=H$, may be prepared from compound (II), such as for example commercially available chroman-4-one. Indeed, compound (II) may be converted into halogen derivative (IIIa), wherein $R_1=R_2=H$ (Scheme 1, step 1), by halogenation-Vilsmeier reaction with an halogenating agents such as POCl$_3$ (phosphorous oxychloride) in the presence of a suitable formamide such as DMF. Compound (IIIa) may be then converted into (IVa), wherein $R_1=R_2=H$, by cross-coupling reactions in the presence of a palladium catalyst like Suzuki coupling with a suitable organoboron reagent (IXa) (SCHEME 1, step 2) and finally to compound (Va) by reduction with an hydride reagent such as sodium borohydride (Scheme 1, step 3).

Similarly, compounds (Vb), wherein $R_1$ and $R_2$ are combined to form an oxo group (=O), $R_3=R_4=H$, can be prepared from compound (IIIb), wherein $R_1$ and $R_2$ are combined to form an oxo group (=O), such as for example commercially available 4-chloro-2-oxo-2H-chromene-3-carbaldehyde. Compound (IIIb) may be then converted into (IVb), wherein $R_1$ and $R_2$ are combined to form an oxo group (=O), by cross-coupling reactions in the presence of a palladium catalyst like Stille coupling with an appropriate organostannane (IXb) (Scheme 1, step 2) finally to compound (Vb) by reduction with an hydride reagent such as sodium borohydride (Scheme 1, step 3).

Compounds (Vc) wherein $R_1=R_2=R_3=H$, $R_4=Me$, can be prepared from compound (IVa), wherein $R_1=R_2=H$, by addition of a Grignard reagent like methylmagnesium bromide (Scheme 1, step 3).

Similarly, compounds (Vd) wherein $R_1$ and $R_2$ are combined to form an oxo group (=O), $R_3=H$, $R_4=Me$ can be prepared from compound (IVb) wherein $R_1$ and $R_2$ are combined to form an oxo group (=O), by addition of a Grignard reagent such as methylmagnesium bromide (Scheme 1, step 3).

Scheme 1.

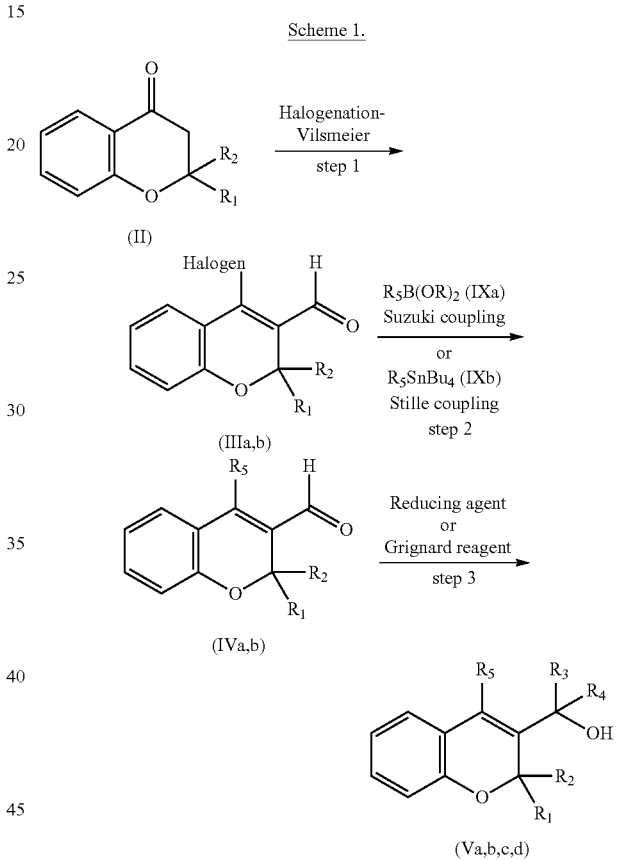

Compounds (Va), wherein $R_1=R_2=R_3=R_4=H$ and compounds (Vc), wherein $R_1=R_2=R_3=H$, $R_4=Me$, may be then converted in (VIa), wherein $R_1=R_2=R_3=R_4=H$, Z=NH and (VIc), wherein $R_1=R_2=R_3=H$, $R_4=Me$, Z=NH by azidation reaction with DPPA (diphenylphosphorylazide) followed by reduction with a suitable reducing agent such as LiAlH$_4$ (Scheme 2). Compounds (Ib), wherein $R_1=R_2=R_3=R_4=H$ and (Ic), wherein $R_1=R_2=R_3=H$, R4=Me were then prepared from compounds (VIa) and (VIc) by reaction with appropriate halogen-containing heterocycle (X) such 4-amino-6-chloropyrimidine-5-carbonitrile and 6-chloro-9H-purine in the presence of an appropriate base like DIEA (Scheme 2). Following this synthetic route compounds 4-amino-6-((4-phenyl-2H-chromen-3-yl)methylamino)pyrimidine-5-carbonitrile (Example 1), N-((4-phenyl-2H-chromen-3-yl)methyl)-9H-purin-6-amine (Example 2), and 4-amino-6-(1-(4-phenyl-2H-chromen-3-yl)ethylamino)pyrimidine-5-carbonitrile (Example 3) were prepared.

Scheme 2.

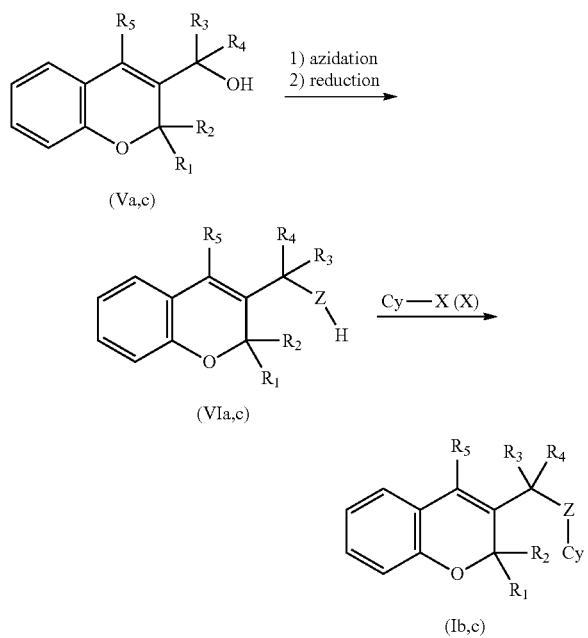

Compound (Id), wherein $R_1$ and $R_2$ are combined to form an oxo group (=O), $R_3$=$R_4$=H, Z=NH, and (Ie), wherein $R_1$ and $R_2$ are combined to form an oxo group (=O), $R_3$=H, $R_4$=Me, Z=NH, may be synthesized as outlined in Scheme 3 from compounds (Vb) and (Vd), that were converted into (VIIb) and (VIId), where the Y represents a leaving group (Lg) such as an halide atom, by reaction with a suitable halogenating agent such as $PBr_3$ and finally reacted with a nitrogen based nucleophile (XI) in the presence of a base like NaH (sodium hydride) (Scheme 3). Following this synthetic route compounds 3-((9H-purin-6-ylamino)methyl)-4-phenyl-2H-chromen-2-one (Example 8) and 3-(1-(9H-purin-6-ylamino)ethyl)-4-phenyl-2H-chromen-2-one (Example 9) were prepared.

Scheme 3.

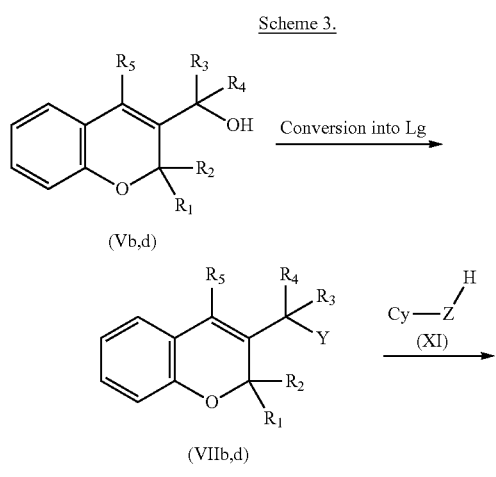

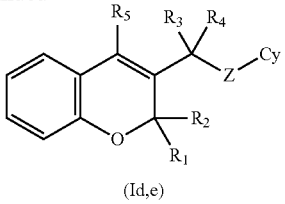

Compound VIIIb, wherein $R_1$ and $R_2$ are combined to form an oxo group (=O) and $R_3$=$R_4$=H, Z is absent and compound VIIId, wherein $R_1$ and $R_2$ are combined to form an oxo group (=O), and $R_3$=H, $R_4$=Me, Z being absent can be synthesized as outlined in Scheme 4 from compounds (Vb) and (Vd), that were converted into (VIIb) and (VIId), where the group Y represents a suitable leaving group such as a halide atom, by reaction with a suitable halogenating agent such as $PBr_3$ and then reacted with commercially available 3-iodo-1H-pyrazolo[3,4-d]pyrimidin-4-amine in the presence of a suitable base like $K_2CO_3$ (Scheme 4, step 1 and 2). Compound (VIIIc), wherein $R_1$=$R_2$=$R_3$=H, $R_4$=Me, Z being absent can be synthesized from compound (Vc), wherein $R_1$=$R_2$=$R_3$=H, $R_4$=Me, by Mitsunobu reaction with a dialkylazadicarboxylate like DIAD (diso-propylazadicarboxylate) in the presence of a phosphine such as $PPh_3$ (triphenylphosphine) and commercially available 3-iodo-1H-pyrazolo[3,4-d]pyrimidin-4-amine (Scheme 4, step 3).

Scheme 4.

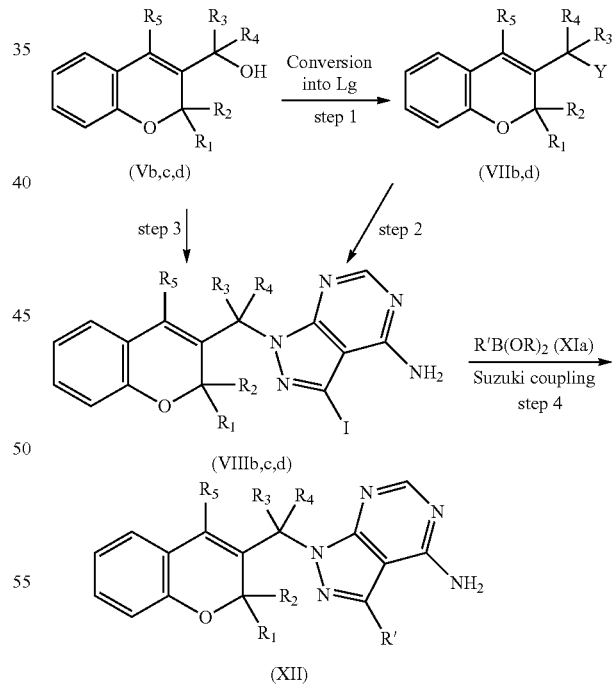

Compounds (VIIIb,c,d) can be further converted into compounds (XII) by means of a Suzuki coupling with a suitable organoboron reagent (XIa) (Scheme E 4, step 4).
Following this synthetic route, compounds:
3-(4-amino-1-(1-(4-phenyl-2H-chromen-3-yl)ethyl)-1H-pyrazolo[3,4-d]pyrimidin-3-yl)-5-chlorophenol (Example 7c), 3-(4-amino-1-(1-(4-phenyl-2H-chromen-2-yl)ethyl)-1H-pyrazolo[3,4-d]pyrimidin-3-yl)-5-hydroxybenzonitrile (Example 7b), 1-(5-(4-amino-1-(1-(4-phenyl-2H-chromen-2-yl)ethyl)-1H-pyrazolo[3,4-d]pyrimidin-3-yl)pyridin-3-yl)-2,2,2-trifluoroethan-1-ol (Example 7a), 3-((4-amino-3-(3-fluoro-5-hydroxyphenyl)-1H-pyrazolo[3,4-d]pyrimidin-1-yl)methyl)-4-phenyl-2H-chromen-2-one (Example 7), 3-(1-(4-amino-3-(3-fluoro-5-hydroxyphenyl)-1H-pyrazolo[3,4-d]pyrimidin-1-yl)ethyl)-4-phenyl-2H-chromen-2-one (Example 6), 3-(4-amino-1-(1-(4-phenyl-2H-chromen-3-yl)ethyl)-1H-pyrazolo[3,4-d]pyrimidin-3-yl)-5-fluorophenol (Example 4), and 5-(4-amino-1-(1-(4-phenyl-2H-chromen-3-yl)ethyl)-1H-pyrazolo[3,4-d]pyrimidin-3-yl)pyridin-3-ol (Example 5) were prepared.

In the particular case when R5 is an heteroaromatic ring substituted with different moieties like for example the 4,4,5,5-tetramethyl-2-(thiophen-2-yl)-1,3-dioxolanyl moiety, compounds XIIb, wherein $R_1=R_2=R_3=H$, R4=Me, Z being absent, can be prepared from compound XIII by a three step sequence (Scheme 5). Compounds XIV can be prepared from compound XII by hydrolysis of the acetal moiety by reaction with an aqueous solution of a mineral acid like HCl (Scheme 5, step 1). Compounds XV wherein $R_1=R_2=R_3=H$, R4=Me, Z being absent and $W=NMe_2$ or N-methylpiperazine or OH can be prepared from compound XIV by reductive amination in the presence of an amine like 1-methylpiperazine or dimethylamine and a suitable hydride donor like sodium triacetoxyborohydride (Scheme 5, step 2). Compounds (XV) wherein $R_1=R_2=R_3=H$, R4=Me, Z being absent and $W=NMe_2$ or N-methylpiperazine or OH can be further converted into compounds (XIIb) by mean of a Suzuki coupling with a suitable organoboron reagent (XIa) (Scheme 5, step 3).

Scheme 5.

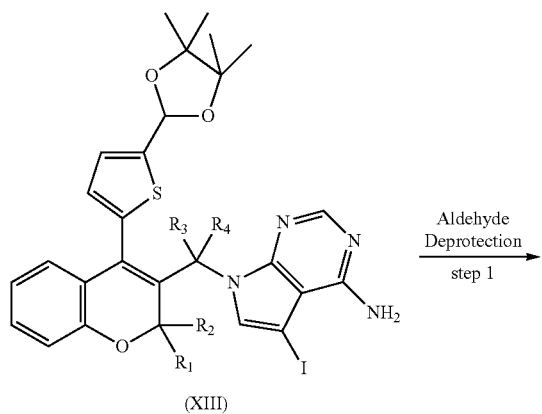

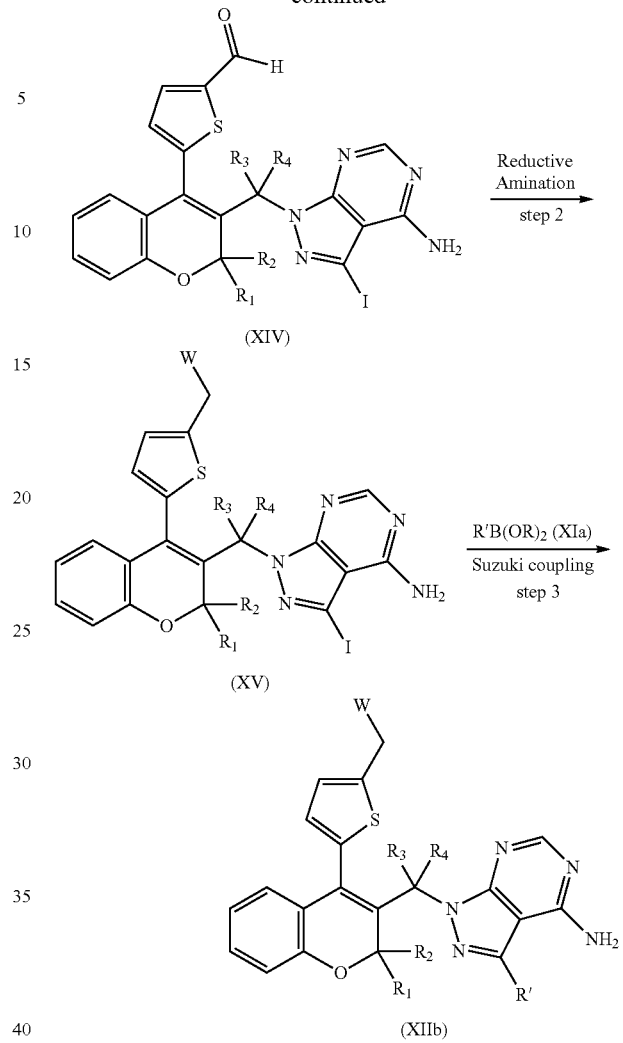

Following this synthetic route, compounds:
3-(4-amino-1-(1-(4-(5-((4-methylpiperazin-1-yl)methyl)thiophen-2-yl)-2H-chromen-3-yl)ethyl)-1H-pyrazolo[3,4-d]pyrimidin-3-yl)-5-fluorophenol (Example 10), 3-(4-amino-1-(1-(4-(5-((dimethylamino)methyl)thiophen-2-yl)-2H-chromen-3-yl)ethyl)-1H-pyrazolo[3,4-d]pyrimidin-3-yl)-5-fluorophenol (Example 11), 3-(4-amino-1-(1-(4-(5-(hydroxymethyl)thiophen-2-yl)-2H-chromen-3-yl)ethyl)-1H-pyrazolo[3,4-d]pyrimidin-3-yl)-5-fluorophenol (Example 12), and 5-(4-amino-1-(1-(4-(5-((dimethylamino)methyl)thiophen-2-yl)-2H-chromen-3-yl)ethyl)-1H-pyrazolo[3,4-d]pyrimidin-3-yl)pyridin-3-ol (Example 13) were prepared.

Some compounds may contain a protected hydroxyl or nitrogen group, such as for example silyl or benzyl ether, which were then removed under well-known procedure.

The compounds of the invention are inhibitors of kinase activity, in particular PI3-kinase activity. Generally speaking, compounds which are PI3K inhibitors may be useful the treatment of many disorders associated with PI3K enzymes mechanisms. Thus they may be used in the manufacture of a medicament for the treatment of said disorders.

In one embodiment, the disorders that can be treated by the compounds of the present invention include respiratory diseases selected from idiopathic chronic cough, cough-variant asthma, cough associated with thoracic tumour or lung cancer, viral or post-viral cough, upper airways cough syndrome (UACS), or post nasal drip cough, or cough associated with gastro-oesophageal reflux disease (both acid and non-acid reflux), asthma, chronic bronchitis, chronic obstructive pulmonary disease (COPD), interstitial lung disease, (such as idiopathic pulmonary fibrosis (IPF)), congestive heart disease, sarcoidosis, infections (such as whooping cough), asthma, chronic obstructive pulmonary disease (COPD) and idiopathic pulmonary fibrosis (IPF); viral infections (including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia, and central pain.

In another embodiment, the disorder that can be treated by the compound of the present invention is selected from the group consisting of idiopathic chronic cough, cough-variant asthma, cough associated with thoracic tumour or lung cancer, viral or post-viral cough, upper airways cough syndrome (UACS), post nasal drip cough, cough associated gastro-oesophageal reflux disease (both acid and non-acid reflux), asthma, chronic bronchitis, chronic obstructive pulmonary disease (COPD) and interstitial lung disease (such as idiopathic pulmonary fibrosis (IPF).

In a further embodiment, the disorder is selected from the group of asthma, chronic obstructive pulmonary disease (COPD), idiopathic pulmonary fibrosis (IPF), cough, and chronic cough.

The methods of treatment of the present invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The present invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention, including such solid forms as tablets, gelcaps, capsules, caplets, granules, lozenges, and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the present invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates, and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the present invention are preferably administered by inhalation.

Inhalable preparations include inhalable powders, propellant-containing metering aerosols, and propellant-free inhalable formulations.

For administration as a dry powder, single- or multi-dose inhalers known from the prior art may be utilized. In that case, the powder may be filled in gelatine, plastic, or other capsules, cartridges or blister packs or in a reservoir.

A diluent or carrier, generally non-toxic and chemically inert to the compounds of the present invention, e.g. lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic, or hydroalcoholic medium, and they may be delivered by jet or ultrasonic nebulizers known from the prior art or by soft-mist nebulizers such as Respimat®.

The compounds of the present invention can be administered as the sole active agent or in combination with other pharmaceutical active ingredients including those currently used in the treatment of respiratory disorders, e.g. beta$_2$-agonists, antimuscarinic agents, corticosteroids mitogen-activated kinases (P38 MAP kinases) inhibitors, nuclear factor kappa-B kinase subunit beta inhibitors (IKK2), human neutrophil elastase (FINE) inhibitors, phosphodiesterase 4 (PDE4) inhibitors, leukotriene modulators, non-steroidal anti-inflammatory agents (NSAIDs), and mucus regulators.

The invention therefore provides pharmaceutical compositions containing the compounds of the present invention in combination with such pharmaceutically active ingredients, in admixture with one or more pharmaceutically acceptable carrier or excipient.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

Other features of the invention will become apparent in the course of the following descriptions of exemplary embodiments which are given for illustration of the invention and are not intended to be limiting thereof.

EXAMPLES

General Experimental Details

Flash chromatography is carried out using an Isolera MPLC system (manufactured by Biotage) using pre-packed silica gel or reverse-phase cartridges (supplied by Biotage).

Many of the compounds described in the following examples have been prepared from stereochemically pure starting materials, for example 95% ee.

The stereochemistry of the compounds in the examples, where indicated, has been assigned on the assumption that absolute configuration at resolved stereogenic centers of staring materials is maintained throughout any subsequent reaction conditions.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Chemical Names of the compounds were generated with Structure To Name Enterprise 10.0 Cambridge Software.
Abbreviations:
Et$_2$O=diethyl ether;
Et$_3$N=triethyl amine;
DMF=dimethylformamide;
EtOAc=ethyl acetate;
RT=room temperature;
THF=tetrahydrofuran;
DCM=dichloromethane;
MeOH=methyl alcohol;
EtOH=ethylic alcohol;
TFA=trifluoroacetic acid;
LC-MS=liquid chromatography/mass spectrometry;
MPLC=medium pressure liquid chromatography;
dppf=1,1'-bis(diphenylphosphino)ferrocene;
S-Phos-Pd-G2=chloro(2-dicyclohexylphosphino-2',6'-dimethoxy-1,1'-biphenyl)[2-(2'-amino-1,1'-biphenyl)]palladium (II);
DIEA=N,N-diisopropylethylamine;
ACN=acetonitrile;
DMSO=dimethylsulfoxide;
UPLC=ultra-performance liquid chromatography.
NMR Characterization:

$^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift. Chemical shifts are reported as δ values in ppm relative to trimethylsilane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).
LC/UV/MS Analytical Methods:
LC/UV/MS—Method 1.

LC instrument: Acquity Waters UPLC (or equivalent) interfaced with 2996 PDA detector
Column: Acquity UPLC BEH C18 1.7 um 50×2.1 mm
Column Temperature (° C.) 30.0
Mobile phases: 95:5 H$_2$O:ACN+(0.1% HCOOH) (A); 5:95 H$_2$O:ACN+(0.1% HCOOH) (B)
Flow (ml/min) 0.6 (split in MS 1:6)
Stop Time (mins) 3.5
Gradient:

| Time (min) | % A | % B |
|---|---|---|
| 0.00 | 100 | 0 |
| 0.50 | 100 | 0 |
| 2.20 | 0.0 | 100.0 |
| 2.70 | 0.0 | 100.0 |
| 2.90 | 100 | 0 |

UV detection: BPI Detection (Start Wavelength nm 210, End Wavelength nm 400, Sampling Rate spectra/sec=20)
Injection Volume (ul)—1.00
Sample solvents: DMSO:MeOH:ACN ratio 1:3:3
LC/UV/MS—Method 2.

LC instrument: Acquity Waters UPLC (or equivalent) interfaced with 2996 PDA detector
Column: Acquity UPLC BEH C18 1.7 um 50×2.1 mm
Column Temperature (° C.) 30.0
Mobile phases: 95:5 H$_2$O:ACN+(0.1% HCOOH) (A); 5:95 H$_2$O:ACN+(0.1% HCOOH) (B)
Flow (ml/min) 0.6 (split in MS 1:6)
Stop Time (mins) 12.0

Gradient:

| Time (min) | % A | % B |
|---|---|---|
| 0.00 | 100 | 0 |
| 0.50 | 100 | 0 |
| 10.0 | 0.0 | 100.0 |
| 11.0 | 0.0 | 100.0 |
| 12.0 | 100 | 0 |

UV detection: BPI Detection (Start Wavelength nm 210, End Wavelength nm 400, Sampling Rate spectra/sec=20)
Injection Volume (ul)—1.00
Sample solvents: DMSO:MeOH:ACN ratio 1:3:3
LC/UV/MS—Method 3 and 3a.
LC instrument: Acquity Waters UPLC (or equivalent) interfaced with 2996 PDA detector
Column: Acquity UPLC CSH C18 1.7 um 130 A 50×2.1 mm
Column Temperature (° C.) 50.0
Mobile phases: HCOONH$_4$ 0.025M pH 3 (A); ACN+0.1% HCOOH (B)
Flow (ml/min) 0.35 (split in MS 1:3 in method 3) (split 1:10 in method 3a)
Stop Time (mins) 10
Gradient:

| Time (min) | % A | % B |
|---|---|---|
| 0.00 | 80 | 20 |
| 5.50 | 20 | 80 |
| 7.5 | 20 | 80 |
| 8 | 80 | 20 |
| 10 | 80 | 20 |

UV detection: BPI Detection (Start Wavelength nm 210, End Wavelength nm 400, Sampling Rate spectra/sec=20)
Injection Volume (ul)—2.00
Sample solvents: H$_2$O/ACN 80/20
LC/UV/MS—Method 4.
LC instrument: Acquity Waters UPLC (or equivalent) interfaced with 2996 PDA detector
Column: Acquity UPLC BEH C18 1.7 um 50×2.1 mm
Column Temperature (° C.) 40.0
Mobile phases: 95:5 H$_2$O:ACN+(0.1% HCOOH) (A); 5:95 H$_2$O:ACN+(0.1% HCOOH) (B)
Flow (ml/min) 1 ml/min
Stop Time (mins) 2
Gradient:

| Time (min) | % A | % B |
|---|---|---|
| 0.00 | 99 | 1 |
| 1.50 | 0.1 | 99.9 |
| 1.90 | 0.1 | 99.9 |
| 2.00 | 99 | 1 |

UV detection: BPI Detection (Start Wavelength nm 210, End Wavelength nm 400, Sampling Rate spectra/sec=20)
Injection Volume (ul)—1.00
LC/UV/MS—Method 5.
UPLC instrument: Waters Acquity
Column: Kinetex 1.7 u PFP 100 A 100×2.1 mm (Phenomenex)
Column Temperature (° C.): 55
Mobile phases: HCOONH$_4$ 0.025M pH 3 (A); ACN (B)
Flow (ml/min): 0.45 (split in MS 1:3)
Stop Time (mins): 10
Gradient:
Time (min) % A % B
Gradient:

| Time (min) | % A | % B |
|---|---|---|
| 0.00 | 85 | 15 |
| 5.00 | 55 | 45 |
| 5.50 | 20 | 80 |
| 6.50 | 20 | 80 |
| 7.00 | 85 | 15 |
| 10.00 | 85 | 15 |

UV detection: DAD
UV acquisition range (nm): 210-400
Injection Volume (μl): 2
Sample Solvent: Acetonitrile
LC/UV/MS—Method 6.
LC instrument: Acquity Waters UPLC (or equivalent) interfaced with 2996 PDA detector
Column: Acquity UPLC CSH C18 1.7 um 130 A 50×2.1 mm
Column Temperature (° C.) 40.0
Mobile phases: 95:5 H$_2$O:ACN+(0.1% HCOOH) (A); 5:95 H$_2$O:ACN+(0.1% HCOOH) (B)
Flow (ml/min) 1 ml/min
Stop Time (mins) 2
Gradient:

| Time (min) | % A | % B |
|---|---|---|
| 0.00 | 99 | 1 |
| 1.50 | 0.1 | 99.9 |
| 1.90 | 0.1 | 99.9 |
| 2.00 | 99 | 1 |

UV detection: BPI Detection (Start Wavelength nm 210, End Wavelength nm 400, Sampling Rate spectra/sec=20)
Injection Volume (ul)—1.00

PREPARATION OF INTERMEDIATES AND EXAMPLES

Intermediate A1:
4-chloro-2H-chromene-3-carbaldehyde

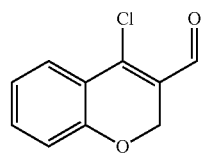

Chroman-4-one (2 g, 13.50 mmol) was dissolved in DCM (45 ml) and DMF (1.6 ml, 20.25 mmol), then POCl$_3$ (3.77 ml, 40.5 mmol) was added drop wise under nitrogen, and the mixture heated at reflux for 6 h and RT overnight. The reaction was diluted with DCM, washed with water, with saturated NaCl$_{aq}$, dried over Na$_2$SO$_4$, and evaporated to dryness. The crude was chromatographed on silica gel with Hexane\EtOAc mixtures to give the title compound (2.1 g, 80% yield) as a yellow solid.

UPLC-MS: 1.99 min, 194.8 [M+H]+, method 1.

Intermediate B1:
4-phenyl-2H-chromene-3-carbaldehyde

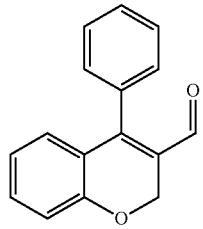 [SMILES: O=CC1=C(c2ccccc2)c2ccccc2OC1]

4-Chloro-2H-chromene-3-carbaldehyde (Intermediate A1, 1 g, 5.14 mmol), phenylboronic acid (0.75 g, 6.17 mmol), and Cs$_2$CO$_3$ (2.0 g, 6.17 mmol) were dissolved DMF (19 ml) and deoxygenated under Argon for 5 min prior to the addition of Pd(PPh$_3$)$_2$Cl$_2$ (0.18 g, 0.257 mmol), then the mixture was heated under nitrogen at 45° C. for 1 h and 4 h at 65° C. The reaction mixture was allowed to cool to RT, partitioned between AcOEt and 1M HCl$_{aq}$, washed twice with water, once with saturated NaCl$_{aq}$, and then the organic layer was dried over Na$_2$SO$_4$ and evaporated to dryness. The crude was chromatographed on silica gel with Hexane\EtOAc mixtures to give the title compound (0.9 g, 74% yield) as yellow solid.

UPLC-MS: 2.14 min, 237.0 [M+H]+, method 1.

Intermediate B2:
2-oxo-4-phenyl-2H-chromene-3-carbaldehyde

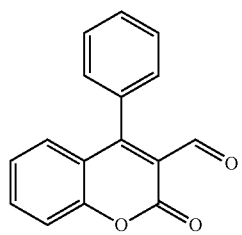 [SMILES: O=Cc1c(-c2ccccc2)c2ccccc2oc1=O]

4-Chloro-2-oxo-2H-chromene-3-carbaldehyde (600 mg, 2.88 mmol), Pd-bis(diphenylphosphine) chloride (202 mg, 0.288 mmol), tributyl(phenyl)stannane (1.47 g, 4.03 mmol), and cesium fluoride (1.31 g, 8.63 mmol) were reacted in dioxane (5.9 ml) at 90° C. for 2 h. The reaction mixture was partitioned between NH$_4$Cl$_{aq}$ (100 ml) and AcOEt (30 ml), the organic layer was washed with Brine, dried over Na$_2$SO$_4$ and dried under reduced pressure to give and the crude was chromatographed on silica gel with Hexane\EtOAc mixtures to give the title compound (407 mg, yield 57%).

UPLC-MS: 4.55 min, 251 [M+H]+, method 2.

Intermediate B3: 4-(5-(4,4,5,5-tetramethyl-1,3-dioxolan-2-yl)thiophen-2-yl)-2H-chromene-3-carbaldehyde

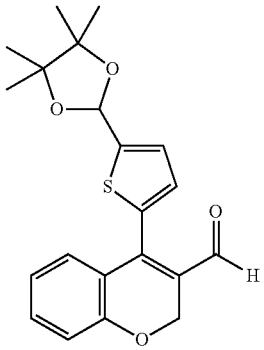 [SMILES: CC1(C)OC(c2ccc(C3=C(C=O)COc4ccccc43)s2)OC1(C)C]

4-chloro-2H-chromene-3-carbaldehyde (Intermediate A1, 3.5 g, 17.98 mmol), 4,4,5,5-tetramethyl-2-(5-(4,4,5,5-tetramethyl-1,3-dioxolan-2-yl)thiophen-2-yl)-1,3,2-dioxaborolane (5.07 g, 14.99 mmol; prepared as described at page 138 of WO 2015/091685, which is incorporated herein by reference in its entirety) and K$_3$PO$_4$ H$_2$O (10.35 g, 45 mmol) were dissolved in THF (100 ml) and water (100 ml). Ar was bubbled for 15 min before the addition of XPhos Pd G2 (0.825 g, 1.049 mmol). Bubbling was continued for further 10 min then the brown turbid mixture was stirred under Ar atm at RT overnight. The mixture was partitioned between ethyl acetate and water, the organic phase anhydrified over sodium sulfate and the solvent evaporated to give the title compound (5.4 g, 97%) of red oil. The crude was used in the following synthetic step without further purification.

UPLC-MS: 2.64 min, 371.2 [(M+H)]+, 272.16 [(M−100)]+, method 6 @

Intermediate C1:
(4-phenyl-2H-chromen-3-yl)methanol

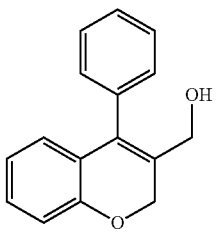 [SMILES: OCC1=C(c2ccccc2)c2ccccc2OC1]

4-Phenyl-2H-chromene-3-carbaldehyde (Intermediate B1, 400 mg, 1.69 mmol) and NaBH$_4$ (256 mg, 6.77 mmol) were reacted in EtOH (8 ml) under nitrogen for 30 min at RT. The reaction was quenched by the addition of 1M HCl$_{aq}$ (10 ml), and the mixture partitioned between AcOEt and 1M HCl$_{aq}$. The organic layer was washed with saturated NaCl$_{aq}$, dried over Na$_2$SO$_4$ and evaporated to dryness to give the title compound (382 mg, 95% yield) as a colourless oil.

UPLC-MS: 1.94 min, 220.9 [(M+H)—H$_2$O]+, method 1.

Intermediate C2:
3-(hydroxymethyl)-4-phenyl-2H-chromen-2-one

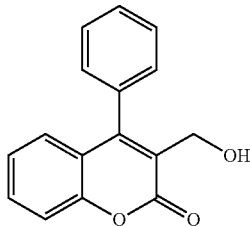 [SMILES: O=c1oc2ccccc2c(-c2ccccc2)c1CO]

2-Oxo-4-phenyl-2H-chromene-3-carbaldehyde (Intermediate B2, 191 mg, 0.763 mmol) and sodium tetrahydroborate (29 mg, 0.763 mmol) were reacted in methanol (7.5 ml) at RT. The reaction mixture was partitioned between AcOEt/NH$_4$Cl$_{aq}$ 5% 1/1 (10 ml). The organic layer was dried over Na$_2$SO$_4$ and dried under reduced pressure to give the title compound (180 mg, 93%) that was used in the next step without any further purification.

UPLC-MS: 1.76 min, 235 [(M+H)—H$_2$O]+, method 1.

Intermediate C3:
1-(4-phenyl-2H-chromen-3-yl)ethanol

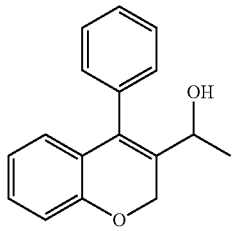 [SMILES: CC(O)C1=C(c2ccccc2)c2ccccc2OC1]

4-Phenyl-2H-chromene-3-carbaldehyde (Intermediate B1, 520 mg, 2.20 mmol) was dissolved in anhydrous THF (8 ml) at 0° C., then methylmagnesium bromide 3M in Et$_2$O (1.47 ml, 4.40 mmol) was added drop wise over 5 min. The mixture was stirred at 0° C. for 15 min, then quenched by the addition of saturated NH$_4$Cl$_{aq}$ and extracted with AcOEt. The organic layer was washed with saturated NaCl$_{aq}$, dried over Na$_2$SO$_4$ and evaporated to dryness to give the title compound (503 mg, 91% yield) as a yellow oil. UPLC-MS: 2.00 min, 234.8 [(M+H)—H$_2$O]+, method 1.

Intermediate C4:
3-(1-hydroxyethyl)-4-phenyl-2H-chromen-2-one

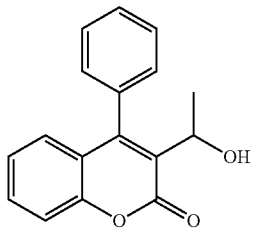 [SMILES: CC(O)c1c(-c2ccccc2)c2ccccc2oc1=O]

2-Oxo-4-phenyl-2H-chromene-3-carbaldehyde (Intermediate B2, 585 mg, 2.34 mmol) and methylmagnesium bromide 3M in THF (0.86 ml, 2.57 mmol) were reacted in dry THF (7.5 ml) at −15° C. for 15 min. The reaction was partitioned between NH$_4$Cl$_{aq}$ (1 ml) and AcOEt (2 ml). Phases were separated, the organic layer was dried over sodium sulfate and evaporated under reduced pressure to afford a crude that was chromatographed on silica gel with Hexane\EtOAc mixtures to give the title compound (250 mg, 40%).

UPLC-MS: 1.06 min, 249 [M+H]+, method 4.

Intermediate C5: 1-(4-(5-(4,4,5,5-tetramethyl-1,3-dioxolan-2-yl)thiophen-2-yl)-2H-chromen-3-yl)ethan-1-ol

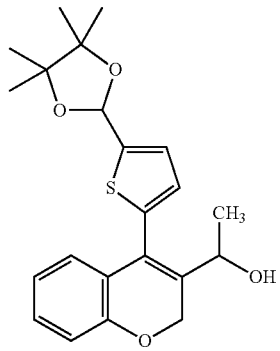 [SMILES: CC(O)C1=C(c2ccc(C3OC(C)(C)C(C)(C)O3)s2)c2ccccc2OC1]

4-(5-(4,4,5,5-tetramethyl-1,3-dioxolan-2-yl)thiophen-2-yl)-2H-chromene-3-carbaldehyde (Intermediate B3, 5.55 g, 14.98 mmol) and methylmagnesium bromide 3M in THF (9.99 ml, 30.0 mmol) were reacted in dry THF (200 ml) at 0° C. for 2 h. The reaction was partitioned between NH$_4$Cl$_{aq}$ (1 ml) and AcOEt (2 ml). Phases were separated, the organic layer was dried over sodium sulfate and evaporated under reduced pressure to afford a crude that was chromatographed on silica gel with Hexane\EtOAc mixtures to give the title compound (5.55 g, 96%).

UPLC-MS: 1.31 min, 369.2 [(M+H)–H$_2$O]+, method 6

Intermediate D1:
3-(bromomethyl)-4-phenyl-2H-chromen-2-one

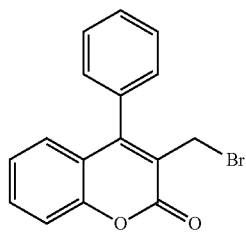 [SMILES: O=c1oc2ccccc2c(-c2ccccc2)c1CBr]

3-(Hydroxymethyl)-4-phenyl-2H-chromen-2-one (Intermediate C2, 160 mg, 0.634 mmol), tribromophosphine 1M in DCM (1.08 ml, 1.08 mmol), were reacted in DCM (1.6 ml) at RT. Solvents were evaporated to give the title compound (239 mg) that was used for next step without any further purification.

UPLC-MS: 2.17 min, 234 [M-Br]+, method 1.

Intermediate D2:
3-(1-bromoethyl)-4-phenyl-2H-chromen-2-one

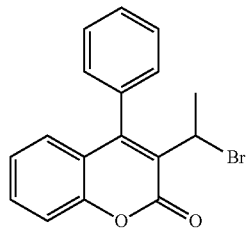 [SMILES: CC(Br)c1c(-c2ccccc2)c2ccccc2oc1=O]

3-(1-Hydroxyethyl)-4-phenyl-2H-chromen-2-one (Intermediate C4, 250 mg, 0.94 mmol) and PBr₃ 1M in DCM (1.57 mg, 1.57 mmol) were reacted in DCM (2.5 ml) at RT for 3 h. The solvent was evaporated under reduced pressure and the crude was purified via reverse phase chromatography with a Biotage C18 30 g SNAP column (Phase A, water 95%, ACN 5%, formic acid 0.1%; Phase B ACN 95%, water 5%, formic acid 0.1%) to give the title compound (203 mg, 66%).

UPLC-MS: 2.24 min, 330.66, 328.66 [(M+H)]+, method 1

Intermediate E1: (4-phenyl-2H-chromen-3-yl)methanamine hydrochloride

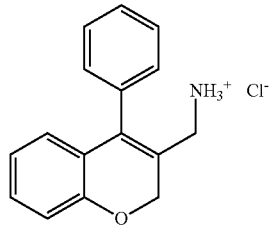 [SMILES: [NH3+]CC1=C(c2ccccc2)c2ccccc2OC1 ; [Cl-]]

(4-phenyl-2H-chromen-3-yl)methanol (Intermediate C1) DBU (0.48 ml, 3.19 mmol) and diphenylphorylazide (0.69 ml, 3.19 mmol) were reacted in THF (8 ml) at RT for 3 h. The reaction mixture was partitioned between water and AcOEt, organic phase washed with 1M HCl$_{aq}$, with saturated NaCl$_{aq}$, dried over Na₂SO₄ and evaporated to dryness. The crude was dissolved in anhydrous THF (10 ml), then a solution 1M of LiAlH₄ in THF (3.19 ml, 3.19 mmol) was added drop wise under nitrogen. The reaction was stirred for 1 h at RT and quenched by the addition of AcOEt and 1M HCl$_{aq}$. The aqueous layer was neutralized with 1M NaOH$_{aq}$ until pH ca 9-10 and extracted twice with AcOEt. The organic layer was dried over Na₂SO₄ and evaporated to dryness. The crude oil was dissolved in Et₂O with 2 ml of 4M HCl in dioxane and the mixture evaporated to dryness to give the title compound (290 mg, 66% yield) as a yellow solid.

UPLC-MS: 1.45 min, 220.9 [(M+H)—NH₃]+, method 1

Intermediate E2: 1-(4-phenyl-2H-chromen-3-yl)ethanamine hydrochloride

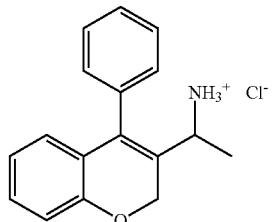

The title compound was prepared analogously to compound of intermediate E1, from 1-(4-phenyl-2H-chromen-3-yl)ethanol (Intermediate C3, 350 mg, 1.39 mmol) to give the title compound (22 mg, 6% yield).

UPLC-MS: 1.55 min, 235.0 [(M+H)—NH3]+, method 1

Intermediate F1: 3-iodo-1-(1-(4-phenyl-2H-chromen-3-yl)ethyl)-1H-pyrazolo[3,4-d]pyrimidin-4-amine

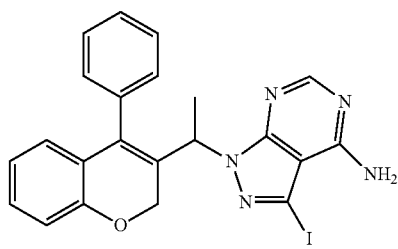 [SMILES: CC(C1=C(c2ccccc2)c2ccccc2OC1)n1nc(I)c2c(N)ncnc21]

(4-Phenyl-2H-chromen-3-yl)ethanol (Intermediate C3 1.60 g, 6.34 mmol), 3-iodo-1H-pyrazolo[3,4-d]pyrimidin-4-amine (1.99 g, 7.61 mmol) and PPh₃ (2.0 g, 7.61 mmol) were stirred in THF (42 ml) for 5 min at RT prior to the drop-wise addition of DIAD (1.22 ml, 6.28 mmol) at 0° C. The reaction was stirred at 0° C. for 5 min and at RT for 1 h, then partitioned between AcOEt and 1M HCl$_{aq}$. The organic layer was washed three times with water, once with saturated NaCl$_{aq}$, dried over Na₂SO₄ and evaporated to dryness. The crude was chromatographed on silica gel with Hexane\EtOAc mixtures to give the title compound (667 mg, 21% yield) as yellowish solid.

UPLC-MS: 1.32 min, 496.0 [M+H]+, method 4

Intermediate F2: 3-(1-(4-amino-3-iodo-1H-pyrazolo[3,4-d]pyrimidin-1-yl)ethyl)-4-phenyl-2H-chromen-2-one

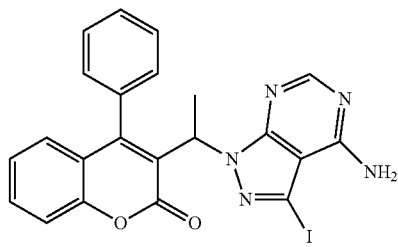 [SMILES: CC(c1c(-c2ccccc2)c2ccccc2oc1=O)n1nc(I)c2c(N)ncnc21]

3-(1-Bromoethyl)-4-phenyl-2H-chromen-2-one (Intermediate D2 101 mg, 0.307 mmol), 3-iodo-1H-pyrazolo[3,4-d]pyrimidin-4-amine (104 mg, 0.40 mmol) and K₂CO₃ (55 m, 0.399 mmol) were reacted in DMF (1 ml) at 60° C. for 18 h. The crude was purified via reverse phase chromatography with a C18 column (Phase A, water 95%, ACN 5%, formic acid 0.1%); Phase B ACN 95%, water 5%, formic acid 0.1%) to give the title compound (75 mg, 48%).

UPLC-MS: 1.15 min, 510 [M+H]+, method 4

Intermediate F3: 3-((4-amino-3-iodo-1H-pyrazolo[3,4-d]pyrimidin-1-yl)methyl)-4-phenyl-2H-chromen-2-one

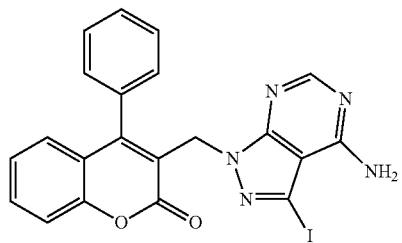 [SMILES: Nc1ncnc2c1c(I)nn2Cc1c(-c2ccccc2)c2ccccc2oc1=O]

3-(Bromomethyl)-4-phenyl-2H-chromen-2-one (Intermediate D1 102 mg, 0.324 mmol), K₂CO₃ (54 mg, 0.40 mmol) and 3-iodo-1H-pyrazolo[3,4-d]pyrimidin-4-amine (101 mg, 0.39 mmol) were reacted in DMF (1.2 ml, 15.50 mmol) at 80° C. for 3 h. The crude was purified via reverse phase chromatography with a C18 column (Phase A, water 95%, ACN 5%, formic acid 0.1%; Phase B ACN 95%, water 5%, formic acid 0.1%) to give the title compound (20 mg, 12.5%).

UPLC-MS: 1.84 min, 496 [M+H]+, method 4.

Intermediate F4: 3-iodo-1-(1-(4-(5-(4,4,5,5-tetramethyl-1,3-dioxolan-2-yl)thiophen-2-yl)-2H-chromen-3-yl)ethyl)-1H-pyrazolo[3,4-d]pyrimidin-4-amine

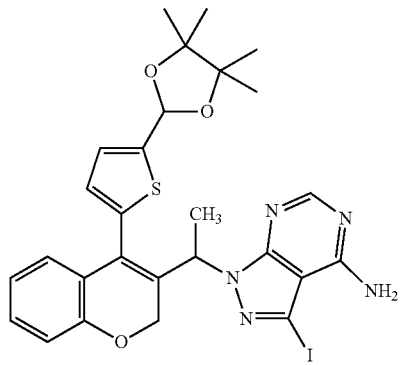 [SMILES: CC(C1=C(c2ccc(C3OC(C)(C)C(C)(C)O3)s2)c2ccccc2OC1)n1nc(I)c2c(N)ncnc21]

1-(4-(5-(4,4,5,5-tetramethyl-1,3-dioxolan-2-yl)thiophen-2-yl)-2H-chromen-3-yl)ethanol (Intermediate C5, 2 g, 5.17 mmol), 3-iodo-1H-pyrazolo[3,4-d]pyrimidin-4-amine (1.621 g, 6.21 mmol) were stirred in THF (42 ml) for 5 min at RT prior to the addition of PPh₃ (1.629 g, 6.21 mmol) then DIAD (1.257 ml 5.17 mmol) at 0° C. The reaction was stirred at 0° C. for 5 min and at RT overnight, then partitioned between AcOEt and saturated NH₄Cl$_{aq}$. The organic layer was washed with saturated NaCl$_{aq}$, dried over Na₂SO₄ and evaporated to dryness. The crude was purified via reverse phase chromatography with a C18 column (Phase A, water 95%, ACN 5%, formic acid 0.1%; Phase B ACN 95%, water 5%, formic acid 0.1%) to give the title compound (193 mg, 5%).

UPLC-MS: 1.46 min, 629.33 [M+H]+, 529.4 [(M+H)–100]+, method 6

Intermediate G1: 5-(3-(1-(4-amino-3-iodo-1H-pyrazolo[3,4-d]pyrimidin-1-yl)ethyl)-2H-chromen-4-yl)thiophene-2-carbaldehyde

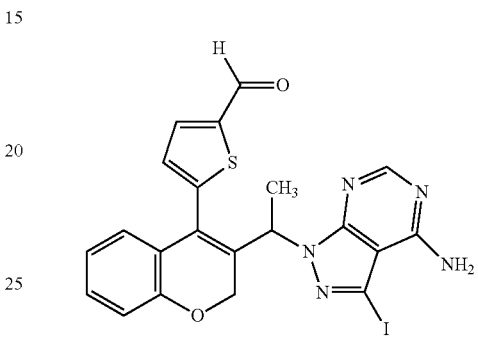

3-iodo-1-(1-(4-(5-(4,4,5,5-tetramethyl-1,3-dioxolan-2-yl)thiophen-2-yl)-2H-chromen-3-yl)ethyl)-1H-pyrazolo[3,4-d]pyrimidin-4-amine (Intermediate F4, 193 mg, 0.307 mmol) was dissolved in ACN (12 mL) and then 1M HCl$_{aq}$ was added till pH<2 and the mixture stirred at RT overnight. ACN was evaporated to give the title product (150 mg, 92%) that was directly used in the next step without further purification.

UPLC-MS: 1.17 min, 529.73 [M+H]+, method 6

Intermediate H1: 3-iodo-1-(1-(4-(5-((4-methylpiperazin-1-yl)methyl)thiophen-2-yl)-2H-chromen-3-yl)ethyl)-1H-pyrazolo[3,4-d]pyrimidin-4-amine

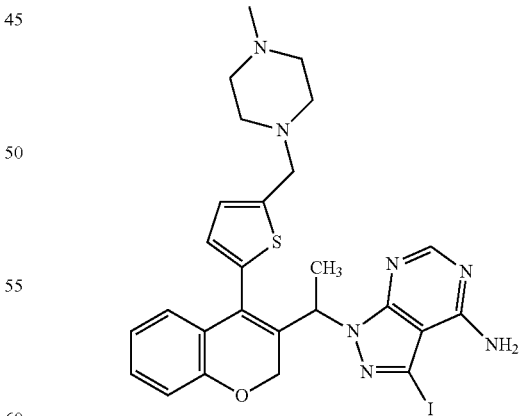

Under a static Ar atmosphere, 5-(3-(1-(4-amino-3-iodo-1H-pyrazolo[3,4-d]pyrimidin-1-yl)ethyl)-2H-chromen-4-yl)thiophene-2-carbaldehyde (Intermediate G1, 162 mg, 0.306 mmol) was suspended in a mixture of DCM\DMF (15 ml\5 mL) then 1-methylpiperazine (0.175 ml, 1.530 mmol), acetic acid (0.088 ml, 1.530 mmol) were added and the mixture stirred at RT for 10 minutes. Sodium triacetoxyhydroborate (0.370 ml, 1.530 mmol) was then added and the mixture was stirred at RT for 4 h. After a further addition of 1-methylpiperazine (0.175 ml, 1.530 mmol), and sodium triacetoxyhydroborate (0.370 ml, 1.530 mmol), the reaction was stirred at RT overnight. Solvent was evaporated, the mixture partitioned between isopropylacetate and a 1M NaOH$_{aq}$., then the organic phase was washed with water and saturated NaCl solution. The solvent was removed and the crude was purified via reverse phase chromatography with a 08 column (Phase A, water 95%, ACN 5%, formic acid 0.1%; Phase B ACN 95%, water 5%, formic acid 0.1%) to give the title compound (42 mg, 22.4%).

UPLC-MS: 0.71 min, 613.70 [M+H]+, method 6

Intermediate H2: 1-(1-(4-(5-((dimethylamino)methyl)thiophen-2-yl)-2H-chromen-3-yl)ethyl)-3-iodo-1H-pyrazolo[3,4-d]pyrimidin-4-amine

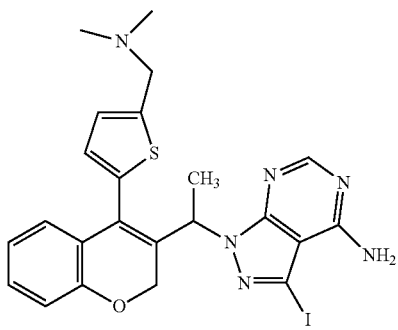 [SMILES: CC(C1=C(c2ccc(CN(C)C)s2)c2ccccc2OC1)n1nc(I)c2c(N)ncnc21]

and

Intermediate H3: (5-(3-(1-(4-amino-3-iodo-1H-pyrazolo[3,4-d]pyrimidin-1-yl)ethyl)-2H-chromen-4-yl)thiophen-2-yl)methanol

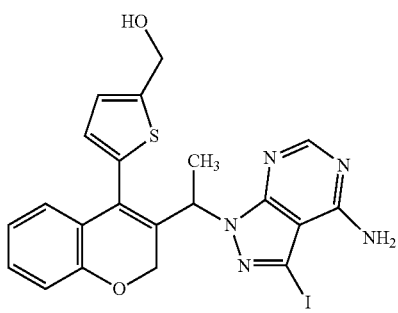 [SMILES: CC(C1=C(c2ccc(CO)s2)c2ccccc2OC1)n1nc(I)c2c(N)ncnc21]

Under a static Ar atmosphere, 5-(3-(1-(4-amino-3-iodo-1H-pyrazolo[3,4-d]pyrimidin-1-yl)ethyl)-2H-chromen-4-yl)thiophene-2-carbaldehyde (Intermediate G1, 177 mg, 0.334 mmol) was suspended in a mixture of DCM\Dioxane\Acetonitrile (15 ml/2.5 ml/2.5 ml) then dimethylamine 2.0 M in THF (0.018 ml, 0.334 mmol), acetic acid (0.096 ml, 1.672 mmol) were added and the mixture stirred at RT for 10 minutes. Then sodium triacetoxyhydroborate (0.404 ml, 1.672 mmol) was added and the mixture was stirred at RT for 4 h. After further addition of dimethylamine 2.0 M in THF (0.018 ml, 0.334 mmol) and sodium triacetoxyhydroborate (0.404 ml, 1.672 mmol), the reaction was stirred at RT overnight. HCl$_{aq}$ 1M was added and the mixture was stirred for 10 min. Organic solvents were removed and the crude was purified via reverse phase chromatography with a C18 column (Phase A, water 95%, ACN 5%, formic acid 0.1%; Phase B ACN 95%, water 5%, formic acid 0.1%) to give Intermediate H2: (58.5 mg, 31%) UPLC-MS: 0.68 min, 558.32 [M+H]+, method 6 and Intermediate H3: (53.5 mg, 30%), UPLC-MS: 1.06 min, 531.47 [M+H]+, method 6

Preparation of Compounds

Example 1. 4-Amino-6-((4-phenyl-2H-chromen-3-yl)methylamino)pyrimidine-5-carbonitrile

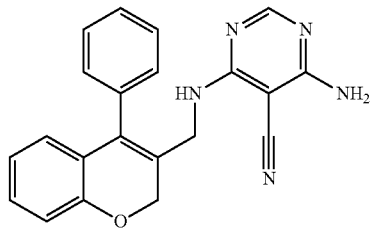 [SMILES: N#Cc1c(N)ncnc1NCC1=C(c2ccccc2)c2ccccc2OC1]

1-(4-Phenyl-2H-chromen-3-yl)methanamine hydrochloride (Intermediate E1 80 mg, 0.292 mmol), 4-amino-6-chloropyrimidine-5-carbonitrile (54 mg, 0.351 mmol) and DIEA (0.10 ml, 0.584 mmol) were reacted in dioxane (15 ml) at 80° C. for 3.5 h, then quenched by the addition of 1M HCl$_{aq}$ (1 ml) The crude was purified via reverse phase chromatography with a Biotage C18 60 g SNAP column (Phase A, water 95%, ACN 5%, formic acid 0.1%); Phase B ACN 95%, water 5%, formic acid 0.1%) to give the title compound (38 mg, 36% yield).

1H NMR (400 MHz, DMSO-d$_6$) δ ppm 7.85 (s, 1H), 7.36-7.57 (m, 4H), 7.05-7.33 (m, 5H), 6.71-6.90 (m, 2H), 6.41-6.58 (m, 1H), 4.68-4.85 (m, 2H), 3.72-4.04 (m, 2H). UPLC-MS: 5.26 min, 356.1 [M+H]+, method 5

Example 2. N-((4-Phenyl-2H-chromen-3-yl)methyl)-9H-purin-6-amine

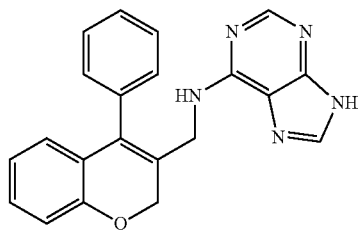 [SMILES: c1ccc(C2=C(CNc3ncnc4[nH]cnc34)COc3ccccc32)cc1]

The title compound was prepared analogously to compound of Example 1, from 1-(4-phenyl-2H-chromen-3-yl)methanamine hydrochloride (Intermediate E1, 80 mg, 0.292 mmol) and 6-chloro-9H-purine (54 mg, 0.351 mmol) to give the title compound (18 mg, 0.051 mmol, 18% yield).

1H NMR (400 MHz, DMSO-d$_6$) δ ppm 12.59-13.04 (bs, 1H), 7.98-8.26 (m, 2H), 7.73-7.91 (m, 1H), 7.28-7.59 (m, 6H), 7.11 (m, 1H), 6.66-6.95 (m, 2H), 6.53 (d, J=7.06 Hz, 1H), 4.82 (s, 2H), 3.99-4.28 (m, 2H).
UPLC-MS: 4.82 min, 356.1 [M+H]+, method 5

Example 3. 4-Amino-6-(1-(4-phenyl-2H-chromen-3-yl)ethylamino)pyrimidine-5-carbonitrile

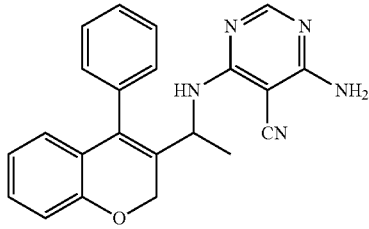 [SMILES: CC(Nc1ncnc(N)c1C#N)C1=C(c2ccccc2)c2ccccc2OC1]

The title compound was prepared analogously to compound of Example 1, from 1-(4-phenyl-2H-chromen-3-yl)ethanamine hydrochloride (Intermediate E2, 20 mg, 0.080 mmol) and 4-amino-6-chloropyrimidine-5-carbonitrile (32 mg, 0.207 mmol) to give the title compound (7 mg, 25% yield) as a white solid.

1H NMR (400 MHz, DMSO-d6) □ ppm 7.95 (s, 1H), 7.34-7.57 (m, 4H), 7.01-7.31 (m, 5H), 6.71-6.89 (m, 2H), 6.34-6.48 (m, 1H), 4.96-5.05 (m, 1H), 4.70-4.82 (m, 1H), 4.54-4.67 (m, 1H), 1.27 (d, J=7.06 Hz, 3H).
UPLC-MS: 5.64 min, 370.1 [M+H]+, method 3a.

Example 4. 3-(4-Amino-1-(1-(4-phenyl-2H-chromen-3-yl)ethyl)-1H-pyrazolo[3,4-d]pyrimidin-3-yl)-5-fluorophenol

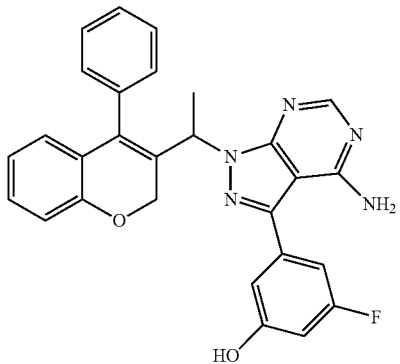 [SMILES: CC(C1=C(c2ccccc2)c2ccccc2OC1)n1nc(-c2cc(O)cc(F)c2)c2c(N)ncnc21]

3-Iodo-1-(1-(4-phenyl-2H-chromen-3-yl)ethyl)-1H-pyrazolo[3,4d]pyrimidin-4-amine (Intermediate F1, 60 mg, 0.121 mmol), (3-fluoro-5-hydroxyphenyl)boronic acid (38 mg, 0.242 mmol), S-Phos Pd G2 (8.73 mg, 0.012 mmol) and K3PO4 H2O (118 mg, 0.363 mmol) were dispersed in THF (2 ml) and deoxygenated under argon for 5 min prior to the addition of water (0.5 ml), and the mixture heated by MW irradiation for 40 min at 85° C. The reaction mixture was diluted with AcOEt and washed twice with water, once with saturated NaCl$_{aq}$, and the organic layer dried over Na2SO4 and dried under reduced pressure. The crude was chromatographed on silica gel with DCM/AcOEt mixtures to give the title compound (37 mg, 64% yield) as a yellowish solid.

1H NMR (400 MHz, DMSO-d6) δ ppm 10.19 (s, 1H), 8.16 (s, 1H), 7.43-7.57 (m, 3H), 7.27 (d, J=7.06 Hz, 2H), 7.06-7.20 (m, 1H), 6.75-6.97 (m, 4H), 6.67 (dt, J=11.03, 2.21 Hz, 1H), 6.47 (dd, J=7.72, 1.54 Hz, 1H), 5.55-5.73 (m, 1H), 4.67-5.23 (m, 2H), 1.66 (d, J=7.06 Hz, 3H).
UPLC-MS: 5.39 min, 480.0 [M+H]+, method 3a.

Example 5. 5-(4-Amino-1-(1-(4-phenyl-2H-chromen-3-yl)ethyl)-1H-pyrazolo[3,4-d]pyrimidin-3-yl)pyridin-3-ol

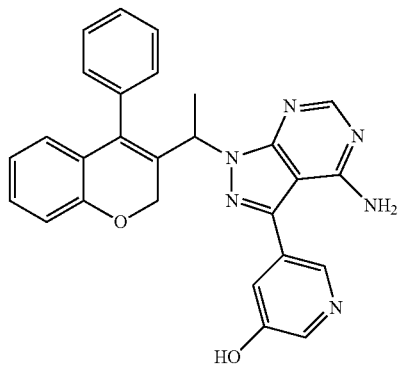 [SMILES: CC(C1=C(c2ccccc2)c2ccccc2OC1)n1nc(-c2cncc(O)c2)c2c(N)ncnc21]

3-Iodo-1-(1-(4-phenyl-2H-chromen-3-yl)ethyl)-1H-pyrazolo[3,4-d]pyrimidin-4-amine (Intermediate F1 (60 mg, 0.121 mmol), 5-(4,4,5,5-tetramethyl-1,3,2-dioxaborolan-2-yl)pyridin-3-ol (53.6 mg, 0.242 mmol), S-Phos Pd G2 (8.73 mg, 0.012 mmol) and K3PO4 H2O (118 mg, 0.363 mmol) were dispersed in THF (2 ml) and deoxygenated under Ar for 5 min prior to the addition of water (0.5 ml), then the reaction was heated under MW irradiation for 80 min at 85° C. Reaction was quenched by the addition of 2M HCl$_{aq}$ (5 ml) and the crude was purified via reverse phase chromatography with a Biotage C18 SNAP column (Phase A, water 95%, ACN 5%, formic acid 0.1%); Phase B ACN 95%, water 5%, formic acid 0.1%) to give the title compound (48 mg, 86% yield) as a yellowish solid.

1H NMR (400 MHz, DMSO-d6) δ ppm 9.98-10.46 (bs, 1H), 8.33 (d, J=1.32 Hz, 1H), 8.22 (d, J=2.65 Hz, 1H), 8.17 (s, 1H), 7.40-7.55 (m, 4H), 7.27 (d, J=6.62 Hz, 2H), 7.14 (m, 1H), 6.74-6.88 (m, 2H), 6.48 (dd, J=7.94, 1.32 Hz, 1H), 5.63 (d, J=7.06 Hz, 1H), 4.57-5.28 (m, 2H), 1.67 (d, J=7.06 Hz, 3H).
UPLC-MS: 4.27 min, 462.9 [M+H]+, method 3a.

Example 6. 3-(1-(4-Amino-3-(3-fluoro-5-hydroxyphenyl)-1H-pyrazolo[3,4-d]pyrimidin-1-yl)ethyl)-4-phenyl-2H-chromen-2-one

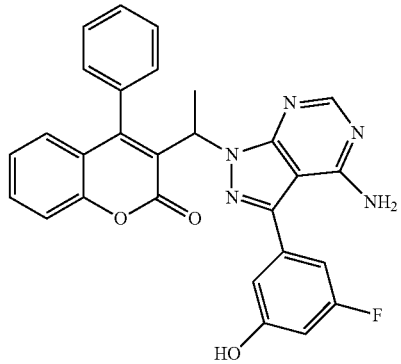 [SMILES: CC(c1c(-c2ccccc2)c2ccccc2oc1=O)n1nc(-c2cc(O)cc(F)c2)c2c(N)ncnc21]

3-(1-(4-Amino-3-iodo-1H-pyrazolo[3,4-d]pyrimidin-1-yl)ethyl)-4-phenyl-2H-chromen-2-one (Intermediate F2 (75 mg, 0.147 mmol), 3-fluoro-5-hydroxyphenylboronic acid (46 mg, 0.295 mmol), PdCl2(dppf) (12.9 mg, 0.018 mmol) and potassium carbonate (41 mg, 0.295 mmol) were reacted in dioxane (730 µl) at 80° C. for 1 h. The crude was purified via reverse phase chromatography with a Biotage C18

SNAP column (Phase A, water 95%, ACN 5%, formic acid 0.1%); Phase B ACN 95%, water 5%, formic acid 0.1%) to give the title compound (62 mg, 85%).

1H NMR (400 MHz, DMSO-d$_6$) δ ppm 10.24 (s, 1H), 8.05 (s, 1H), 7.58-7.66 (m, 1H), 7.33-7.53 (m, 5H), 7.17-7.28 (m, 1H), 6.91-6.96 (m, 1H), 6.79-6.83 (m, 1H), 6.69-6.79 (m, 2H), 6.59-6.67 (m, 1H), 5.52-5.73 (m, 1H), 1.79-2.00 (m, 3H).

UPLC-MS: 4.45 min, 494 [M+H]+, method 3

Example 7. 3-((4-Amino-3-(3-fluoro-5-hydroxyphenyl)-1H-pyrazolo[3,4-d]pyrimidin-1-yl)methyl)-4-phenyl-2H-chromen-2-one

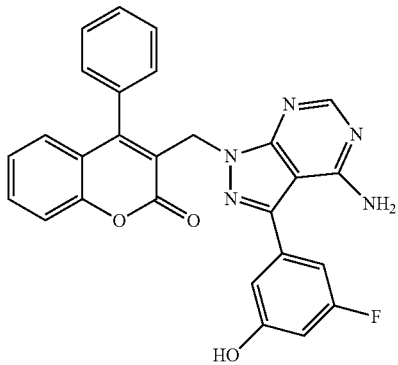 [SMILES: Nc1ncnc2c1c(-c1cc(O)cc(F)c1)nn2Cc1c(-c2ccccc2)c2ccccc2oc1=O]

3-((4-Amino-3-iodo-1H-pyrazolo[3,4-d]pyrimidin-1-yl)methyl)-4-phenyl-2H-chromen-2-one (Intermediate F3 (20 mg, 0.04 mmol)), 3-fluoro-5-hydroxyphenylboronic acid (12.6 mg, 0.08 mmol), cesium carbonate (26.3 mg, 0.08 mmol) and Pd(PPh$_3$)$_4$ (3.7 mg, 3.23 μmol) were reacted in DMF (200 μl) under microwave irradiation at 120° C. for 1 h. The crude was purified via reverse phase chromatography with a Biotage C18 SNAP column (Phase A, water 95%, ACN 5%, formic acid 0.1%); Phase B ACN 95%, water 5%, formic acid 0.1%) to give the title compound (9 mg, 47%).

1H NMR (400 MHz, DMSO-d$_6$) δ ppm 8.14 (s, 1H), 7.18-7.75 (m, 15H), 5.36 (s, 2H)

UPLC-MS: 4.00 min, 480 [M+H]+, method 3

Example 7a. 1-(5-(4-amino-1-(1-(4-phenyl-2H-chromen-2-yl)ethyl)-1H-pyrazolo[3,4-d]pyrimidin-3-yl)pyridin-3-yl)-2,2,2-trifluoroethan-1-ol

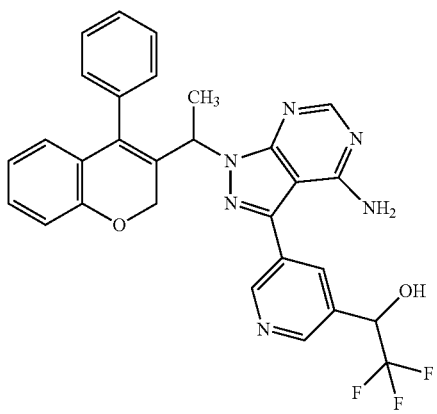 [SMILES: CC(C1=C(c2ccccc2)c2ccccc2OC1)n1nc(-c2cncc(C(O)C(F)(F)F)c2)c2c(N)ncnc21]

3-iodo-1-(1-(4-phenyl-2H-chromen-3-yl)ethyl)-1H-pyrazolo[3,4-d]pyrimidin-4-amine (Intermediate F1 (50 mg, 0.101 mmol)), 2,2,2-trifluoro-1-(5-(4,4,5,5-tetramethyl-1,3,2-dioxaborolan-2-yl)pyridin-3-yl)ethanol (92 mg, 0.303 mmol) and K$_3$PO$_4$ H$_2$O (70 mg, 0.303 mmol) were dispersed in THF (3.75 ml) and deoxygenated under Ar for 5 min prior to the addition of water (1.25 ml). Reaction was heated at 70° C. and then S-Phos Pd G2 (7.27 mg, 10.09 μmol) was added. The reaction was stirred for 30 min. The mixture was then quenched with 1M HClaq, the solvent evaporated and the residue submitted to reverse phase chromatography crude was purified via reverse phase chromatography with a Biotage C18 SNAP column (Phase A, water 95%, ACN 5%, formic acid 0.1%); Phase B ACN 95%, water 5%, formic acid 0.1%) to yield the title compound (0.042 g, 0.072 mmol, 71.6% yield) as a yellow solid.

$^1$H NMR (400 MHz, DMSO-d$_6$) δ ppm 8.83-8.94 (m, 1H), 8.67-8.81 (m, 1H), 8.14-8.27 (m, 2H), 7.42-7.62 (m, 3H), 7.23-7.35 (bs, 2H), 7.09-7.21 (m, 2H), 6.69-6.92 (m, 2H), 6.42-6.58 (m, 1H), 5.56-5.74 (m, 1H), 5.33-5.54 (m, 1H), 5.00-5.23 (m, 1H), 4.67-4.87 (m, 1H), 1.58-1.86 (m, 3H)

UPLC-MS: 1.19 min, 545 [M+H]+, method 6.

Example 7b. 3-(4-amino-1-(1-(4-phenyl-2H-chromen-2-yl)ethyl)-1H-pyrazolo[3,4-d]pyrimidin-3-yl)-5-hydroxybenzonitrile

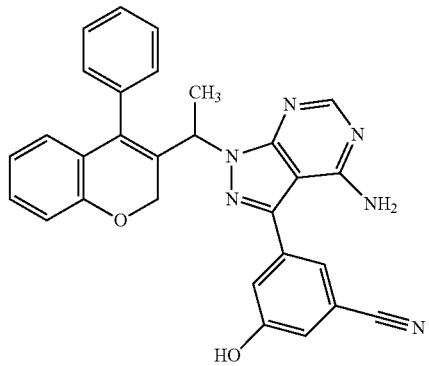 [SMILES: CC(C1=C(c2ccccc2)c2ccccc2OC1)n1nc(-c2cc(O)cc(C#N)c2)c2c(N)ncnc21]

The title compound was prepared analogously to compound of Example 7, from 3-iodo-1-(1-(4-phenyl-2H-chromen-3-yl)ethyl)-1H-pyrazolo[3,4-d]pyrimidin-4-amine (Intermediate F1 (30 mg, 0.061 mmol)), 3-hydroxy-5-(4,4,5,5-tetramethyl-1,3,2-dioxaborolan-2-yl)benzonitrile (45 mg, 0.182 mmol), K$_3$PO$_4$ H$_2$O (42 mg, 0.182 mmol) and SPhos Pd G2 (4.36 mg, 6.06 μmol) to give the title compound (7.8 mg, 0.016 mmol, 26.5% yield) as a yellow solid.

$^1$H NMR (400 MHz, DMSO-d$_6$) δ ppm 10.30-10.61 (bs, 1H), 8.05-8.23 (m, 1H), 7.42-7.59 (m, 4H), 7.33-7.42 (m, 1H), 7.19-7.33 (m, 3H), 7.07-7.19 (m, 1H), 6.71-6.87 (m, 2H), 6.38-6.53 (m, 1H), 5.57-5.71 (m, 1H), 4.67-5.22 (m, 2H), 1.61-1.72 (m, 3H)

UPLC-MS: 1.26 min, 487.2 [M+H]+, method 6.

Example 7c. 3-(4-amino-1-(1-(4-phenyl-2H-chromen-3-yl)ethyl)-1H-pyrazolo[3,4-d]pyrimidin-3-yl)-5-chlorophenol

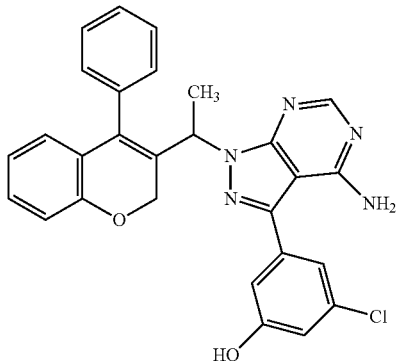 [SMILES: CC(C1=C(c2ccccc2)c2ccccc2OC1)n1nc(-c2cc(O)cc(Cl)c2)c2c(N)ncnc21]

The title compound was prepared analogously to compound of Example 7, from 3-iodo-1-(1-(4-phenyl-2H-chromen-3-yl)ethyl)-1H-pyrazolo[3,4-d]pyrimidin-4-amine (Intermediate F1 (30 mg, 0.061 mmol), 3-chloro-5-(4,4,5,5-tetramethyl-1,3,2-dioxaborolan-2-yl)phenol (15 mg, 0.061 mmol), $K_3PO_4\cdot H_2O$ (42 mg, 0.182 mmol) and SPhos Pd G2 (4.36 mg, 6.06 μmol) to give the title compound (10.7 mg, 0.022 mmol, 35.6% yield) as a yellow solid.

$^1$H NMR (400 MHz, DMSO-$d_6$) δ ppm 10.09 (s, 1H), 8.15 (s, 1H), 7.36-7.60 (m, 3H), 7.22-7.34 (m, 2H), 7.08-7.17 (m, 2H), 6.99-7.08 (m, 1H), 6.72-6.94 (m, 3H), 6.40-6.53 (m, 1H), 5.44-5.71 (m, 2H), 1.56-1.76 (m, 3H) UPLC-MS: 1.37 min, 496.1 [M+H]+, method 6.

Example 8. 3-((9H-Purin-6-ylamino)methyl)-4-phenyl-2H-chromen-2-one

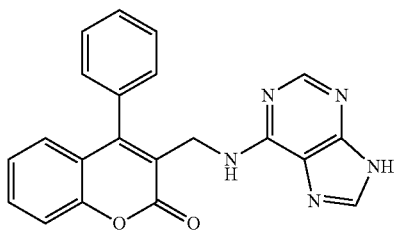 [SMILES: O=c1oc2ccccc2c(-c2ccccc2)c1CNc1ncnc2[nH]cnc12]

Tert-butyl 9-trityl-9H-purin-6-ylcarbamate (70 mg, 0.222 mmol) and 50% dispersion in mineral oil NaH (9.7 mg, 0.244 mmol) were dissolved in DMF (0.5 ml) at 0° C. A solution of 3-(bromomethyl)-4-phenyl-2H-chromen-2-one (Intermediate D1 (73 mg, 0.143 mmol) in DMF (0.5 ml) was then added. The reaction mixture was stirred at 0° C. for 5 min and at 80° C. for 1 h. The reaction mixture was then diluted with EtOAc (20 ml) and washed with 0.2 M HCl, sat NaCl, dried over $Na_2SO_4$ and concentrated under reduced pressure. TFA (1.5 ml) in DCM (2 ml) was added and the mixture stirred for 1 h then dried under reduced pressure to give a crude that was purified via reverse phase chromatography with a Biotage C18 30 g SNAP column (Phase A, water 95%, ACN 5%, formic acid 0.1%); Phase B ACN 95%, water 5%, formic acid 0.1%) to give the title compound (4 mg, 5%).

1H NMR (400 MHz, DMSO-$d_6$) δ ppm 12.73-12.98 (bs, 1H), 7.98-8.16 (m, 2H), 7.36-7.70 (m, 8H), 7.18-7.35 (m, 1H), 6.89-7.05 (m, 1H), 4.00-4.59 (m, 2H)

UPLC-MS: 1.69 min, 370 [M+H]+, method 1

Example 9. 3-(1-(9H-Purin-6-ylamino)ethyl)-4-phenyl-2H-chromen-2-one

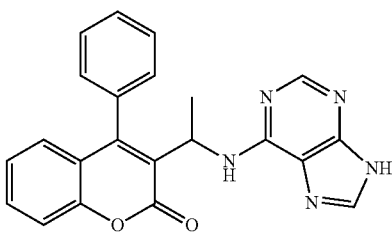 [SMILES: CC(Nc1ncnc2[nH]cnc12)c1c(-c2ccccc2)c2ccccc2oc1=O]

The title compound was prepared analogously to compound of Example 8, from 3-(1-bromoethyl)-4-phenyl-2H-chromen-2-one (Intermediate D2 (63 mg, 0.191 mmol) and tert-butyl 9-trityl-9H-purin-6-ylcarbamate (101 mg, 0.21 mmol) to give the title compound (18 mg, 25%).

1H NMR (400 MHz, DMSO) δ ppm 13.64-13.85 (bs, 1H), 8.74-9.07 (m, 2H), 8.33-8.56 (m, 4H), 8.11-8.32 (m, 3H), 8.01-8.11 (m, 1H), 7.77-7.90 (m, 1H), 7.65-7.73 (m, 1H), 5.75-6.17 (m, 1H), 2.20-2.52 (m, 3H).

UPLC-MS: 3.47 min, 384 [M+H]+, method 3

Example 10. 3-(4-amino-1-(1-(4-(5-((4-methylpiperazin-1-yl)methyl)thiophen-2-yl)-2H-chromen-3-yl)ethyl)-1H-pyrazolo[3,4-d]pyrimidin-3-yl)-5-fluorophenol

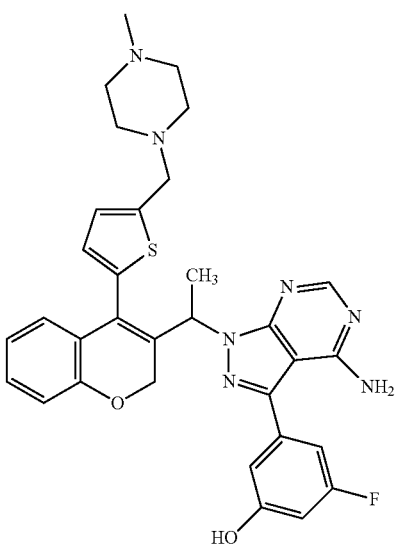 [SMILES: CC(C1=C(c2ccc(CN3CCN(C)CC3)s2)c2ccccc2OC1)n1nc(-c2cc(O)cc(F)c2)c2c(N)ncnc21]

3-fluoro-5-hydroxyphenylboronic acid (10.67 mg, 0.068 mmol), 3-iodo-1-(1-(4-(5-((4-methylpiperazin-1-yl)methyl)thiophen-2-yl)-2H-chromen-3-yl)ethyl)-1H-pyrazolo[3,4-d]pyrimidin-4-amine (Intermediate H1, 42 mg, 0.068 mmol) and potassium phosphate hydrate (47.3 mg, 0.205 mmol) were dispersed in THF (3.75 ml) and deoxygenated under Ar for 5 min prior to the addition of water (1.25 ml). Reaction was heated at 70° C. and then S-Phos Pd G2 (7.27 mg, 10.09 μmol) was added. The reaction was stirred for 3 h, before the addition of further equivalents of catalyst and base. The reaction was stirred for other 3 h at 70° C. The mixture was then quenched with 1M HClaq, the solvent evaporated and the residue submitted to reverse phase chromatography crude was purified via reverse phase chromatography with a Biotage C18 SNAP column (Phase A, water 95%, ACN 5%, formic acid 0.1%); Phase B ACN 95%, water 5%, formic acid 0.1%) to yield the title compound (12.8 mg, 31.3% yield) as a white solid.

$^1$H NMR (400 MHz, DMSO-$d_6$) δ ppm 10.04-10.33 (m, 1H), 8.15 (d, J=7.9 Hz, 2H), 6.55-7.26 (m, 10H), 5.84-6.00 (m, 1H), 4.63-5.15 (m, 2H), 3.55-3.85 (m, 2H), 2.33 (m, 8H), 2.16 (s, 3H), 1.68 (d, J=7.0 Hz, 3H).

UPLC-MS: 0.75 min, 598.16 [M+H]+, method 6.

Example 11. 3-(4-amino-1-(1-(4-(5-((dimethyl-amino)methyl)thiophen-2-yl)-2H-chromen-3-yl)ethyl)-1H-pyrazolo[3,4-d]pyrimidin-3-yl)-5-fluorophenol

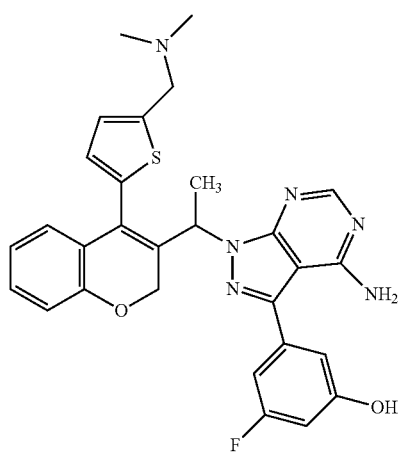 [SMILES: CC(C1=C(c2ccc(CN(C)C)s2)c2ccccc2OC1)n1nc(-c2cc(O)cc(F)c2)c2c(N)ncnc21]

The title compound was prepared analogously to compound of Example 7, from 1-(1-(4-(5-((dimethylamino)methyl)thiophen-2-yl)-2H-chromen-3-yl)ethyl)-3-iodo-1H-pyrazolo[3,4-d]pyrimidin-4-amine (Intermediate H2, 60 mg, 0.107 mmol), 3-fluoro-5-hydroxyphenylboronic acid (16.75 mg, 0.107 mmol), potassium phosphate hydrate (74.2 mg, 0.322 mmol) and SPhos Pd G2 (7.74 mg, 10.74 μmol) to give the title compound (3.7 mg, 6.3% yield) as a yellow solid.

$^1$H NMR (400 MHz, DMSO-$d_6$) δ ppm 10.17 (s, 1H) 7.12-7.19 (m, 1H) 6.92 (s, 1H) 6.80-6.90 (m, 4H) 6.77 (br d, J=7.89 Hz, 2H) 6.65 (br d, J=10.09 Hz, 1H) 6.48 (s, 1H) 5.88 (br d, J=7.45 Hz, 1H) 5.10 (d, J=14.47 Hz, 1H) 4.81 (br d, J=14.47 Hz, 1H) 3.63 (s, 2H) 1.67 (d, J=7.45 Hz, 3H)

UPLC-MS: 0.70 min, 542.78 [M+H]+, method 6.

Example 12. 3-(4-amino-1-(1-(4-(5-(hydroxymethyl)thiophen-2-yl)-2H-chromen-3-yl)ethyl)-1H-pyrazolo[3,4-d]pyrimidin-3-yl)-5-fluorophenol

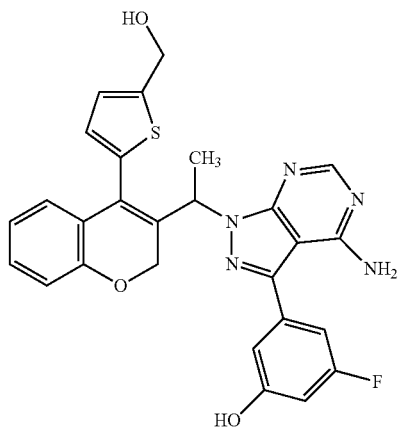 [SMILES: CC(C1=C(c2ccc(CO)s2)c2ccccc2OC1)n1nc(-c2cc(O)cc(F)c2)c2c(N)ncnc21]

The title compound was prepared analogously to compound of Example 7, from (5-(3-(1-(4-amino-3-iodo-1H-pyrazolo[3,4-d]pyrimidin-1-yl)ethyl)-2H-chromen-4-yl)thiophen-2-yl)methanol (Intermediate H3, 53.5 mg, 0.101 mmol), 3-fluoro-5-hydroxyphenylboronic acid (47.1 mg, 0.302 mmol) potassium phosphate hydrate (69.6 mg, 0.302 mmol) and SPhos Pd G2 (7.26 mg, 10.07 μmol) to give the title compound (10.0 mg, 19.6% yield).

$^1$H NMR (400 MHz, DMSO-$d_6$) δ ppm 10.05-10.36 (bs, 1H), 8.20 (s, 1H), 6.47-7.25 (m, 11H), 5.89 (d, J=7.0 Hz, 1H), 5.55 (br. s., 1H), 5.13 (d, J=14.9 Hz, 1H), 4.19-4.82 (m, 3H), 1.71 (d, J=7.5 Hz, 3H)

UPLC-MS: 1.03 min, 515.93 [M+H]+, method 6.

Example 13. 5-(4-amino-1-(1-(4-(5-((dimethyl-amino)methyl)thiophen-2-yl)-2H-chromen-3-yl)ethyl)-1H-pyrazolo[3,4-d]pyrimidin-3-yl)pyridin-3-ol

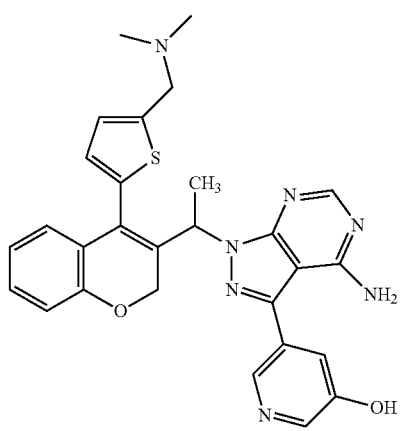 [SMILES: CC(C1=C(c2ccc(CN(C)C)s2)c2ccccc2OC1)n1nc(-c2cncc(O)c2)c2c(N)ncnc21]

The title compound was prepared analogously to compound of Example 7, from 1-(1-(4-(5-((dimethylamino)methyl)thiophen-2-yl)-2H-chromen-3-yl)ethyl)-3-iodo-1H-pyrazolo[3,4-d]pyrimidin-4-amine (Intermediate H2, 30 mg, 0.054 mmol), 5-(4,4,5,5-tetramethyl-1,3,2-dioxaborolan-2- yl)pyridin-3-ol (35.6 mg, 0.161 mmol), potassium phosphate hydrate (37.1 mg, 0.161 mmol) and SPhos Pd G2 (3.87 mg, 5.37 µmol) to give the title compound (28.2 mg, 11.7% yield) as a solid.

Pharmacological Activity of the Compounds of the Present Invention:

In Vitro Determination of the PI3K Enzyme Inhibitory Activity in the Cell Free Assay.

Human recombinant proteins PI3Kα, PI3Kβ, PI3Kγ, and PI3Kδ were purchased from Millipore Ltd (Billerica, Mass.). Compounds were dissolved at 0.5 mM in DMSO and were tested at different concentrations for their activity against PI3Ks using the ADP-Glo™ Kinase Assay (Promega, Madison Wis.) according to the manufacturer's instructions.

Briefly, the kinase reactions were performed in 384-well white plates (Greiner Bio-One GmbH, Frickenhausen). Each well was loaded with 0.1 µl of test compounds and 2.5 µl of 2× reaction buffer (40 mM Tris pH7.5, 0.5 mM EGTA, 0.5 mM $Na_3VO_4$, 5 mM β-glycerophosphate, 0.1 mg/ml BSA, 1 mM DTT), containing 50 µM PI and PS substrates (L-α-phosphatidylinositol sodium salt and L-α-phosphatidyl-L-serine, Sigma-Aldrich, St. Louis Mo.) and the PI3K recombinant proteins (PI3Kγ 0.25 ng/µl, PI3Kδ1 ng/µl, PI3Kα 0.125 ng/µl, and PI3Kβ 1 ng/µl).

The reactions were started by adding 2.5 µl of 2×ATP solution to each well (final concentrations: PI3Kγ ATP 30 µM; PI3Kδ ATP 80 µM; PI3Kα ATP 50 µM; PI3Kβ ATP 100 µM) and incubated for 60 min at room temperature. Subsequently, each kinase reaction was incubated for 40 min with 5 µADP-Glo™ Reagent, allowing depletion of unconsumed ATP. Then, the Kinase Detection Reagent (10 µl) was added in each well to convert ADP to ATP and to allow the newly synthesized ATP to be measured using a luciferase/luciferin reaction. Following 60 min incubation, the luminescence signal was measured using a Wallac EnVision® multilabel reader (PerkinElmer, Waltham Mass.). Curve fitting and IC50 calculation were carried out using a four-parameter logistic model in XLfit (IDBS, Guilford, UK) for Microsoft Excel (Microsoft, Redmont, Wash.).

Compounds of the present invention showed an IC50 lower than 1 µM with respect to the PI3K-delta subunit, preferably lower than 100 nM.

In Vitro Determination of the PI3K Enzyme Inhibitory Activity in the PBMCs Assay.

Human peripheral blood mononuclear cells (PBMCs) were purchased from Lonza (Basel, CH), washed and resuspended in RPMI 1640 medium (w/o Phenol Red) supplemented with 10% FBS, 2 mM glutamine, 100 U/ml penicillin and 100 µg/mL streptomycin (Life Technologies, Carlsbad Calif.). PBMCs were plated at a density of $10^5$ cells/well in 96-well plates coated with 6 µg/ml anti-human CD3 antibody (Biolegend, San Diego Calif.).

Cells were treated in RPMI (w/o Phenol Red) supplemented with 10% FBS with different concentrations of PI3K inhibitors ($10^{-12}$M-$10^{-5}$M, final DMSO concentration 0.2%), co-stimulated with 3 µg/ml anti-human CD28 antibody (BD Biosciences, San Jose Calif.) and incubated for 72 h in an atmosphere of 95% air and 5% CO2 at 37° C. Human IL-6 and IL-17 were measured in the supernatants using paired antibody quantitative ELISA kits (from Life Technologies, Carlsbad Calif. and R&D Systems, Minneapolis Minn. respectively) according to the manufacturer's instructions. IC50 values were determined from concentration-response curves by nonlinear regression analysis using the Graph Pad Prism v.6 (GraphPad Software, La Jolla Calif.).

Compounds of the present invention showed an IC50 lower than 1 µM with respect to the PI3K-delta subunit.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

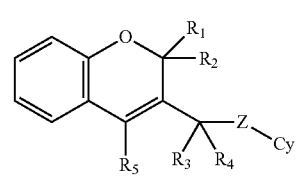

wherein:
$R_1$ and $R_2$ are both H or are combined to form an oxo group (=O);
$R_3$ and $R_4$, are the same or different, and in each occurrence are H, ($C_1$-$C_6$) alkyl, or ($C_1$-$C_6$) haloalkyl;
$R_5$ is phenyl or 2-, 3-, 4- or 5-thienyl, each of which is optionally substituted by one or more groups selected from the group consisting of ($C_1$-$C_6$) alkyl, ($C_1$-$C_6$) hydroxyalkyl, and substituted or unsubstituted ($C_1$-$C_6$) aminoalkyl;
Z is absent or NH; and
Cy is 9H purin-6-yl, 1H-pyrazolo[3,4-d]pyrimidin-1-yl, or 6-pyrimidinyl, each of which is optionally substituted by one or more groups selected from the group consisting of halogen, CN, $NR_{10}R_{11}$, optionally substituted phenyl, and optionally substituted 2-, 3-, 4-, 5-, and 6-pyridinyl;
$R_{10}$ and $R_{11}$ are the same or different, and at each occurrence are independently H, ($C_1$-$C_6$) aminoalkyl, ($C_1$-$C_6$) hydroxyalkyl, or ($C_1$-$C_6$) alkyl, or taken together with the nitrogen atom to which they are linked, $R_{10}$ and $R_{11}$ form, a 5 to 6 membered heterocyclic radical,
or a pharmaceutically acceptable salt thereof.

2. A compound or salt according to claim 1, represented by formula (IA):

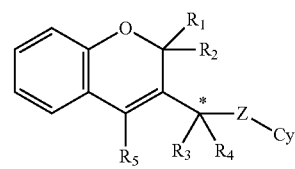

wherein $R_3$ is ($C_1$-$C_6$) alkyl, or ($C_1$-$C_6$) haloalkyl, $R_4$ is H, and the absolute configuration of the chiral carbon (*) is (R) or (S).

3. A compound or salt according to claim 1, wherein:
$R_1$ and $R_2$ are both H or are combined to form an oxo group (=O);
$R_3$ is H or ($C_1$-$C_6$) alkyl;
$R_4$ is H;
$R_5$ is substituted or unsubstituted aryl or substituted or unsubstituted heteroaryl; and
Z, is absent or NH.

4. A compound or salt according to claim 1, wherein:
$R_1$ and $R_2$ are both H or are combined to form an oxo group (=O);
$R_3$ is H, methyl, ethyl, or propyl; and
$R_4$ is H.

5. A compound or salt according to claim 1 wherein:
$R_1$ and $R_2$ are both H or are combined to form an oxo group (=O);
$R_3$ is H, methyl, ethyl, or propyl;
$R_4$ is H; and
$R_5$ is phenyl, 2-, 3-, 4- or 5-thienyl each of which is optionally substituted by one or more groups selected from the group consisting of 4-piperazinomethyl, (4-methylpiperazin-1-yl)methyl, piperidin-1-ylmethyl, hydroxymethyl, dimethylaminomethyl, and (3-(hydroxymethyl)azetidin-1-yl)methyl.

6. A compound or salt according to claim 1, wherein:
$R_1$ and $R_2$ are both H or are combined to form an oxo group (=O);
$R_3$ is H, methyl, ethyl, or propyl;
$R_4$ is H;
Cy is 9H purin-6-yl, 1H-pyrazolo[3,4-d]pyrimidin-1-yl, or 6-pyrimidinyl, each of which is optionally substituted by one or more groups selected from the group consisting of halogen, CN, $NR_{10}R_{11}$, optionally substituted phenyl, and optionally substituted 2-, 3-, 4-, 5-, and 6-pyridinyl;
$R_{10}$, $R_{11}$, are the same or different, and at each occurrence are independently H, ($C_1$-$C_6$) aminoalkyl, ($C_1$-$C_6$) hydroxyalkyl, or ($C_1$-$C_6$) alkyl, or taken together with the nitrogen atom to which they are linked, $R_{10}$ and $R_{11}$ form, a 5 to 6 membered heterocyclic radical.

7. A compound or salt according to claim 1, wherein:
$R_1$ and $R_2$ are both H or are combined to form an oxo group (=O);
$R_3$ is H, methyl, or ethyl;
$R_4$ is H;
$R_5$ is phenyl, or 2-, 3-, 4- or 5-thienyl, each of which are optionally substituted by one or more groups selected from the group consisting of 4-piperazinomethyl, (4-methylpiperazin-1-yl)methyl, piperidin-1-ylmethyl, hydroxymethyl, dimethylaminomethyl, and (3-(hydroxymethyl)azetidin-1-yl)methyl;
Cy is 9H-purin-6-yl, 1H-pyrazolo[3,4-d]pyrimidin-1-yl, or 2-, 4-, 5- or 6-pyrimidinyl, each of which is optionally substituted by one or more groups selected from the group consisting of Cl, Br, F, I, —CN, $NH_2$, 3-fluoro-5-hydroxyphenyl, 3-chloro-5-hydroxyphenyl, 3-cyano-5-hydroxyphenyl, hydroxy-pyridyl, and (2,2,2-trifluoro-1-(pyridin-3-yl)ethanol)5yl.

8. A compound or salt according to claim 1, wherein:
$R_1$ and $R_2$ are both H;
$R_3$ is H, methyl, or ethyl;
$R_4$ is H;
Z is absent;
Cy is 1H-pyrazolo[3,4-d]pyrimidin-1-yl, optionally and independently substituted by one or more groups selected from the group consisting of halogen, $NR_{10}R_{11}$, ($C_1$-$C_6$) alkyl, substituted or unsubstituted aryl, and substituted or unsubstituted heteroaryl.

9. A compound or salt according to claim 1, wherein:
$R_1$ and $R_2$ are both 1-1;
$R_3$ is H, methyl, or ethyl;
$R_4$ is H;
$R_5$ is phenyl, or 2-, 3-, 4- or 5-thienyl, each of which is optionally substituted by one or more substituted or unsubstituted ($C_1$-$C_6$) aminoalkyl groups;
Z is absent;
Cy is 1H-pyrazolo[3,4-d]pyrimidin-1-yl, optionally substituted by one or more groups selected independently from the group consisting of halogen, $NR_{10}R_{11}$, phenyl, and pyridinyl, wherein said phenyl and pyridinyl groups are optionally and independently substituted by one or more groups selected from the group consisting of halogen, —OH, —CN; $NR_{10}R_{11}$ ($C_1$-$C_6$)-haloalkyl, and ($C_1$-$C_6$) hydroxyalkyl;
$R_{10}$, $R_{11}$, the same or different, and are at each occurrence independently H, ($C_1$-$C_6$) aminoalkyl, ($C_1$-$C_6$) hydroxyalkyl, or ($C_1$-$C_6$) alkyl, or taken together with the nitrogen atom to which they are linked, $R_{10}$ and $R_{11}$ form a 5 to 6 membered heterocyclic radical.

10. A compound or salt according to claim 1, wherein:
$R_1$ and $R_2$ are both H or are combined to form an oxo group (=O);
$R_3$ is H or methyl;
$R_4$ is H;
$R_5$ is phenyl or thienyl, wherein each of said phenyl or thienyl groups are optionally substituted by a group selected from the group consisting of substituted or unsubstituted ($C_1$-$C_6$) aminoalkyl and ($C_1$-$C_6$) hydroxyalkyl;
Cy is 9H-purin-6-yl, 1H-pyrazolo[3,4-d]pyrimidin-1-yl, or 2-, 4-, 5- or 6-pyrimidinyl, each of which is optionally substituted by one or more groups selected from the group consisting of CN, $NH_2$ 3-fluoro-5-hydroxyphenyl, 3-chloro-5-hydroxyphenyl 3-cyano-5-hydroxyphenyl, and 3-hydroxy-5-pyridyl, (2,2,2-trifluoro-1-(pyridin-3-yl)ethanol)5yl.

11. A compound or salt, which is a chromene compound selected from the group consisting of:
3-((4-amino-3-(3-fluoro-5-hydroxyphenyl)-1H-pyrazolo[3,4-d]pyrimidin-1-yl)methyl)-4-phenyl-2H-chromen-2-one;
3-(1-(4-amino-3-(3-fluoro-5-hydroxyphenyl)-1H-pyrazolo[3,4-d]pyrimidin-1-yl)ethyl)-4-phenyl-2H-chromen-2-one;
3-(4-amino-1-(1-(4-phenyl-2H-chromen-3-yl)ethyl)-1H-pyrazolo[3,4-d]pyrimidin-3-yl)-5-fluorophenol;
5-(4-amino-1-(1-(4-phenyl-2H-chromen-3-yl)ethyl)-1H-pyrazolo[3,4-d]pyrimidin-3-yl)pyridin-3-ol;
3-((9H-purin-6-ylamino)methyl)-4-phenyl-2H-chromen-2-one;
3-(1-(9H-purin-6-ylamino)ethyl)-4-phenyl-2H-chromen-2-one;
N-((4-phenyl-2H-chromen-3-yl)methyl)-9H-purin-6-amine;
4-amino-6-((4-phenyl-2H-chromen-3-yl)methylamino)pyrimidine-5-carbonitrile;
4-amino-6-(1-(4-phenyl-2H-chromen-3-yl)ethylamino)pyrimidine-5-carbonitrile;
1-(5-(4-amino-1-(1-(4-phenyl-2H-chromen-2-yl)ethyl)-1H-pyrazolo[3,4-d]pyrimidin-3-yl)pyridin-3-yl)-2,2,2-trifluoroethan-1-ol;

3-(4-amino-1-(1-(4-phenyl-2H-chromen-2-yl)ethyl)-1H-pyrazolo[3,4-d]pyrimidin-3-yl)-5-hydroxybenzonitrile;

3-(4-amino-1-(1-(4-phenyl-2H-chromen-3-yl)ethyl)-1H-pyrazolo[3,4-d]pyrimidin-3-yl)-5-chlorophenol;

3-(4-amino-1-(1-(4-(5-((4-methylpiperazin-1-yl)methyl)thiophen-2-yl)-2H-chromen-3-yl)ethyl)-1H-pyrazolo[3,4-d]pyrimidin-3-yl)-5-fluorophenol;

3-(4-amino-1-(1-(4-(5-((dimethylamino)methyl)thiophen-2-yl)-2H-chromen-3-yl)ethyl)-1H-pyrazolo[3,4-d]pyrimidin-3-yl)-5-fluorophenol;

3-(4-amino-1-(1-(4-(5-(hydroxymethyl)thiophen-2-yl)-2H-chromen-3-yl)ethyl)-1H-pyrazolo[3,4-d]pyrimidin-3-yl)-5-fluorophenol; and 5-(4-amino-1-(1-(4-(5-((dimethylamino)methyl)thiophen-2-yl)-2H-chromen-3-yl)ethyl)-1H-pyrazolo[3,4-d]pyrimidin-3-yl)pyridin-3-ol or pharmaceutically acceptable salt of said chromene compound.

12. A pharmaceutical composition, comprising a compound or salt according to claim 1 in admixture with one or more pharmaceutically acceptable carriers or excipients.

13. A pharmaceutical composition, comprising a compound or salt according to claim 1 in combination with one or more active ingredients selected from the group consisting of a beta$_2$-agonist, an antimuscarinic agent, a corticosteroid, a mitogen-activated kinase (P38 MAP kinases) inhibitor, a nuclear factor kappa-B kinase subunit beta inhibitor (IKK2), a human neutrophil elastase (HNE) inhibitor, a phosphodiesterase 4 (PDE4) inhibitor, a leukotriene modulator, a non-steroidal anti-inflammatory agent (NSAID), and a mucus regulator, in admixture with one or more pharmaceutically acceptable carrier or excipient.

14. A method for the treatment of asthma, chronic obstructive pulmonary disease, or idiopathic pulmonary fibrosis, said method comprising administering, to a subject in need thereof, an effective amount of a compound or salt according to claim 1.

15. A method for the treatment of asthma, chronic obstructive pulmonary disease, or idiopathic pulmonary fibrosis, said method comprising administering, to a subject in need thereof, an effective amount of a compound or salt according to claim 11.

16. A pharmaceutical composition, comprising a compound or salt according to claim 11 in admixture with one or more pharmaceutically acceptable carriers or excipients.

17. A pharmaceutical composition, comprising a compound or salt according to claim 11 in combination with one or more active ingredients selected from the group consisting of a beta$_2$-agonist, an antimuscarinic agent, a corticosteroid, a mitogen-activated kinase (P38 MAP kinases) inhibitor, a nuclear factor kappa-B kinase subunit beta inhibitor (IKK2), a human neutrophil elastase (HNE) inhibitor, a phosphodiesterase 4 (PDE4) inhibitor, a leukotriene modulator, a non-steroidal anti-inflammatory agent (NSAID), and a mucus regulator, in admixture with one or more pharmaceutically acceptable carrier or excipient.

\* \* \* \* \*